(12) United States Patent
Pellegretti

(10) Patent No.: US 6,749,569 B1
(45) Date of Patent: Jun. 15, 2004

(54) METHOD AND APPARATUS FOR ULTRASOUND IMAGING

(75) Inventor: Paolo Pellegretti, Genoa (IT)

(73) Assignee: Esaote S.p.A., Casale Monferrato (IT)

( * ) Notice: Subject to any disclaimer, the term of this patent is extended or adjusted under 35 U.S.C. 154(b) by 0 days.

(21) Appl. No.: 10/337,707

(22) Filed: Jan. 7, 2003

(51) Int. Cl.[7] .............................................. A61B 8/00
(52) U.S. Cl. ...................................................... 600/441
(58) Field of Search ................................. 600/437–472; 367/7, 11, 130, 138; 128/916; 424/9.51, 9.52; 73/620–633

(56) References Cited

U.S. PATENT DOCUMENTS 5,724,974 A * 3/1998 Goodsell et al. ............ 600/453

* cited by examiner

Primary Examiner—Ali Imam
(74) Attorney, Agent, or Firm—Woodard, Emhardt, Moriarty, McNett & Henry LLP

(57) ABSTRACT

A method for ultrasound imaging of tissues located in a tissue image region includes the steps of projecting at least one ultrasound beam into the tissue image region and receiving ultrasound reflections in order to transduce the ultrasound reflections into corresponding electric echo signals. The echo signals are processed according to at least two different modes including, an imaging mode for furnishing a panoramic image of the region under examination and a second processing mode that is a different echo processing mode for imaging particular tissues or tissue structures. The images obtained by processing are displayed on the same screen wherein the image obtained by the first mode is displayed with a gray scale and the image obtained by the second mode is displayed in a colored manner.

144 Claims, 10 Drawing Sheets

METHOD AND APPARATUS FOR ULTRASOUND IMAGING

BACKGROUND OF THE INVENTION

The invention relates to a method for ultrasound imaging of tissues located in a tissue image region, that includes the steps of:
a) Projecting at least an ultrasound beam into the tissues image region;
b) Receiving ultrasound reflections of the at least one projected ultrasound beam from the tissue image region and transducing the reflection into corresponding electrical echo signals;
c) Processing the echo signals according to at least two different modes;
d) One of the processing modes being an imaging mode furnishing a panoramic image of the region under examination;
e) The other at least further processing mode being a different processing mode for imaging particular tissues or tissue structures or physiological flows.

Different modes of evaluating the ultrasound beams reflections for reconstructing useful diagnostic images of internal tissues are known and used in the ecographic imaging devices.

Each different mode has been developed for achieving useful diagnostic images of the internal tissues. Particularly recent imaging modes lead to images which evidence the pathology searched but only for the specific tissue without combining this visual information with a general view or panoramic view of the region where the particular tissue is located or embedded. This gives rise to difficulties in driving the apparatus in a correct way, since the user normally brings the ultrasound probe manually in position at the body to be examined. In absence of a general view of the region under examination the user has no way to orientates itself in order to find the correct position of the probe for taking an image of the tissue to be imaged.

This situation gets worse if one considers that most of the alternative imaging modes such as Doppler or power Doppler modes and all the so called Harmonic Imaging modes leads to a signal only with a certain delay and in some cases also only when the specific tissue is correctly pointed by the scanning beams emitted by the probe.

Furthermore, the actual imaging modes are all separately exploited. So many advantages residing in the mutual integration of the information which may be extracted by the different modes from the reflected signals are lost.

From the point of view of the treatment of digital images a combination of the information of two or more images of the same object may be a simple way to solve the problem. However in the case of diagnostic images the problem lays in the fact that not each kind of combination may lead to the construction of an image having improved information content for diagnostic examinations.

A further problem which renders the use of combined imaging techniques less interesting consists in the fact that in order to allow simple and effective examinations and to obviate to the actual difficulties of the user in correctly handling and moving the probe, a real time output of the images is aimed. This requires very high acquisition and/or computing rates and thus expensive hardware configurations. In order to limit the expense normally a compromise is chosen which depending on the imaging mode may lead to a so called quasi real time output of the images, i.e. to image information extraction and image reconstruction times which are relatively short in order to resemble roughly to a real time function.

As it might be understood from the above there are two technical problems which solutions contrast one against the other in the sense that a solution of one of the said problems means a worsening of the conditions for solving the other problem.

The present invention aims to solve the aforementioned problems by providing a method for ultrasound imaging of tissues which allows to produce better or more complete images of tissues from the point of view of the intelligible information brought to evidence therewith and having better visual appearance.

A further object of the present invention is to provide for particular embodiments of the aforementioned method which may be useful for extracting special information from the images acquired.

The inventions solves the above mentioned problems with a method for ultrasound imaging as described above which comprises in combination the following steps:
h) Displaying the images obtained by processing with the at least two modes in an interleaved or combined, particularly superimposed manner on the same screen;
i) The B-mode image being displayed with a black and white or gray- scale image;
j) The image of the at least one further processing mode being displayed in a colored manner by choosing a color adapted to the optimum physiological capability of human eyes to discriminate the information displayed by the color level scale.

In a preferred embodiment method the color chosen is within the green to yellow wavelengths interval.

Using this kind of combination the information according to the different imaging modes gives the possibility of viewing at the same time or in a same image a particular object which may be successfully or better revealed by a special or particular imaging mode and region in which this object is embedded.

In moving the probe during scanning the user may have the possibility to know at every moment where he is directing the probe within the body under examination and may rapidly correct the probe position and/or orientation if this two parameters have not been correctly chosen. This reduces the examination duration particularly when the examination requires invasive techniques such as Harmonic Imaging with injection in the region to be imaged of a contrast medium. Indeed this medium will rest in the region to be imaged and in the particular object to be examined only for a predetermined and limited period of time.

The said B-mode image may be reconstructed from reflected beams at the fundamental frequency of the projected beams or at a subharmonic or harmonic frequency of the projected beams (Harmonic B-mode Imaging).

The second processing mode may be any kind of signal processing actual or future and for example it may be a mode using physical effects on the reflected echo signals such as frequency shifts or changes in the frequency spectra of the reflected echo signals as for example the so called Pulse Inversion imaging mode.

According to the so called Pulse Inversion mode two successive beams are projected into the region under examination for each scanning line the second beam being inverted with respect to the first beam. The two reflected beams due to the two projected beams are then summed together. Other kind of combination of differentiation of the reflected beams due to two or more successive projected beams along the same scan line may be used and are known in the art.

An alternative second processing mode is a so called Harmonic Imaging mode, being the echo signals received at a different frequency of the fundamental frequency of the projected ultrasound beam and/or being extracted from the echo signals the part of said echo signals within a certain frequency spectrum or having a certain frequency different from the fundamental frequency of the ultrasound beam projected. Particularly reflected echo signals having an harmonic or subharmonic frequency, commonly a frequency corresponding to the second harmonic of the fundamental frequency of the projected ultrasound beam are used.

Alternatively also the so called Doppler o Power Doppler modes may be used as the second processing or imaging mode.

As it might appear from the above, the mentioned processing or imaging modes are not limited to the use as a second imaging mode, the images reconstructed therewith are used to be combined with the images resulting from the first processing or Imaging mode. Indeed it is possible to use also as a first processing or imaging mode one of the above imaging modes indicated for the second processing or imaging mode.

It is also clear that a further development of the present invention may consist in processing or reconstructing images from the received reflected beams according to three or more different processing or imaging modes of the kinds listed above.

In this case many combinations of modes may be achieved and many way of displaying and combining the corresponding images are possible.

According to a first example of combination of the images obtained by the three different imaging modes, there are displayed alternatively or side by side at least two or three images relating to the combination of the information of the first and second processing mode and of the first and third processing mode and or of the second and third processing mode.

In this case there might be an automatic time sharing program of the display monitor for each image or a manual selection by the user.

A further option may consist in the fact at least two of the three combination images are displayed adjacent to one another in different areas of the display screen, while the third combination image is displayed alternatively to one of the first two images either by automatic time sharing of the display or by manual command.

Alternatively the three combination images are displayed at the same time in partial areas of the display screen.

Another feature consists in the fact that the first processing or imaging mode is a so called B-mode, the second processing or imaging mode is a so called Harmonic Imaging mode or Pulse Inversion mode, the third processing mode is a so called Doppler or Color Doppler or Power Doppler mode.

In this case at least two. of the three combination images are displayed relating to the combination of the information of the B-mode and of the Harmonic Imaging or Pulse inversion mode and according the combination of information of the B-mode and the Doppler or Color Doppler or Power Doppler mode. A third image is obtained from the combination of information of the Harmonic Imaging Mode or the Pulse Inversion Mode and of the information of the Doppler, or Colour Doppler or Power Doppler mode and may be displayed either with the preceding two combination images or with one of the preceding two images, or alone.

Other combinations may be used as well as the combinations of a first mode, as the B-mode with one of two further different modes which are different also one with respect to the other.

Also the kind of combination of two modes may be executed in different ways.

One first way of combining the information or the images of the at least two imaging modes according to the present invention consists in the fact that the two images are simply superimposed.

According to a further improvement the image displayed is a weighted combination of the image processed with a first processing mode and of the image processed with at least a second processing mode.

As an example of a weighted combination the following algorithm may be used:

alpha*first-mode+(1-alfa)*second-mode with alpha being variable between 0 and 1.

A further way of combining the information or images according at least two imaging modes consists in modulating some parameters of the image of a first processing mode by means of the information obtained by the at least one second processing mode.

Color images on the display are formed by an ensemble or an array of luminous dots. In a black and white matrix of such dots, called pixels, the value corresponds to the intensity of the pixel which variation defines a gray-scale from white to black. Using the signals to drive the display obtained by the B-mode Imaging process leads to an image in gray-scale. The signal corresponding to a scanning line, and thus to a reflected beam has a structure variable in time and time is correlated to the depths of penetration of the signal in the examined body. Thus by means of the velocity of propagation of sound in the body it is possible to univocally correlate the level of the reflected signal related to this line at a certain moment to a certain depth. Thus by digitalizing the signal corresponding to a reflected beam it is possible to construct a vector in which signal intensity is correlated to the depth. This vector is then transformed in driving signals of pixels of a pixel matrix aligned on a line and each pixel or group of pixels along this line will be driven at an intensity or luminosity, i.e. at a white, gray or black level corresponding to the signal level of the vector components. In this case it may be said that the image data obtained by the B-mode drives the value of the pixels.

It is to be stressed that the example with the line is made in order to facilitate comprehension but it is easy to understand that this concept may be applied also considering a two-dimensional matrix corresponding to several adjacent lines or to a three-dimensional matrix.

Such a gray-scale or black and white image may then be colored. In order to color a black and white or gray scale image two parameters are available. First of all it is possible to give a range in which the color may vary. It is possible to chose only one color such as a yellow, green or blue -scale or a range extending over wavelength corresponding to more colors. Technically this parameter is called the Hue and it defines the kind of color. Driving this parameter does not mean that the image is colored but that if it will be colored the range will be that defined by the chosen Hue parameter. The second parameter makes sure that the image is colored according to the hue defined. This parameter is called saturation and it gives the level of presence of color. If the saturation is zero we still have a gray-scale or black and white image. By increasing the saturation to the gray scale the colors are mixed according to the hue that has been chosen. Very low values of saturation will color the gray-scale image weakly as if a colored transparency has been superimposed on the black and white or gray-scale image. Higher levels of saturation will cover more and more the gray-scale or black and white image which becomes a fully colored image. Thus this coloring method may be used in such a way as to combine the information of the two imaging modes in order to display an image that intuitively depicts the situation relating to the information acquired by the second imaging or processing mode from the region under examination or from only a part of it.

According to the present invention a way of combining the information or images of the two imaging modes consists in displaying the image by means of a Hue-Saturation-Value transform (HSV) by defining a constant value for Hue at a wavelength at which human eye's sensitivity is higher, particularly in the green to yellow wavelength range, and by modulating the Value by means of the information obtained with a first processing mode (particularly a B-mode) and by modulating the saturation by means of the information obtained with a second processing mode (as for example Harmonic Imaging mode).

This means that the first imaging mode gives a pure black and white or gray-scale image of the scanned region while the information of second imaging mode is displayed by the color defined through the constant hue range and the appearance of the color on the black and white or gray-scale image is more or less present depending on the level of the image data according to the second imaging mode.

Considering for example a B-mode image of an interesting region, this method will display a gray-scale image of the region. Typically for example in human tissues the B-mode image depicts very good the substantially stationary tissues and corresponds to a general view of the region under. examination which is scanned.

When a second Imaging mode is used for imaging for example contrast media perfusion/vascular flow, such as Harmonic imaging, Pulse inversion or Two or more Pulse combination modes the data obtained by these modes will determine the more or less color presence defined by the hue range chosen. This color will appear only in the zones of the image where a blood flow/contrast perfusion exists and the color saturation may indicate the intensity or density or the blood flow/contrast perfusion. Thus the combined image obtained does not.give only intuitive information about the existence of a bloodflow/contrast perfusion and the location of the flow/perfusion in a region under examination, but also gives intuitively understandable information about the intensity and/or density and or velocity of the flow/perfusion. This information may be read directly from the graphical appearance of the image displayed.

Instead of a HSV palette a HIS or a HLS palette may be used for forming an image displaying at the same time the information obtained from a first and from a second imaging or processing mode.

When three imaging or processing modes are considered instead of only two, such as for example a B-mode Imaging, Harmonic Imaging and Doppler or Power Doppler imaging, the third imaging or processing mode may be used for driving the Hue range thus adding more information. In this case Doppler or Power Doppler imaging for example of vascular or other physiological flows are measures of the velocity or intensity of movement and a different color may be associated with different velocities or movements intensities of the flow, while the saturation driven by the Harmonic Imaging mode gives a measure of the amount of contrast. media in each resolution cell Another way to combine the information of two images modes consists in applying a palette representation based on a Hue-Saturation-Value (HSV) transform, which uses Hue= constant (corresponding to a wavelength at which human eye's sensibility is higher, that is, chosen in the green/yellow wavelengths' interval), Saturation=Contrast channel and Value=alfa*B-Mode+(1-alfa)*Contrast Defined as the above the Value channel can be considered as an information from B-Mode modulated by the Contrast on the basis of the weight parameter "alfa". The effect to adopt such a representation is to have a color image of the Contrast with in transparency visualized B-Mode. The effect of a transparency is controlled by "alfa", that is alfa=0 means no transparency, alfa=1 means full transparency.

Choosing a proper value for "alfa" would allow to have the desired underlying B-Mode information In a more general embodiment we can imagine to mix three different information sources (e.g. B-Mode, Harmonic B-Mode, Doppler) by driving with their proper linear/non linear combinations the three channels of an HIS, HSV, HLS palette.

All the above mentioned steps of the method according to the invention do not consider the way with which the reflected beams are generated and the way to process them.

According to a first embodiment or option of the method of the present invention, the different imaging modes are used for evaluating the signals of the same reflected beam being originated by the same projected beam focussed along one scan-line in a predetermined scan-plane or slice of the region under examination.

In this case the digitalized signals may be processed in parallel by two or more signal processing channels which are optimized for a specific imaging mode of the two or more imaging or processing modes provided. Such a parallel processing option of the received signals for each imaging or processing mode has the advantage to be very fast but requires physically two signal processing channels and determines increased hardware costs.

Alternatively or in combination with the above option in the particular case of more than two imaging modes, only one signal processing channel may be provided which is driven by multiplexing in order to process the received signals according to the different imaging modes. In this case the need for hardware is reduced, however, in order to optimize the processing channel for processing the signals according to each of the imaging modes, a more flexible hardware is needed which may also be capable of saving in a memory different parameters setting for the different imaging modes. These parameter settings must be loaded in the hardware each time the multiplexing protocol addresses a different imaging mode.

When more than two imaging modes are provided it is important to understand that there might be only two processing channels which may be driven in parallel for processing two of the three processing modes and by multiplexing the input of the two channels between the two processing modes and the third one.

The above mentioned options may be also applied in combination with a. further improvement of the method which comprises that for each imaging method an optimized projecting beam is generated which causes a corresponding reflected beam optimized for one of the imaging modes provided. The two or more projected beams, depending on the number of chosen different processing modes which needs an optimized projected beam are fired one after the other with a short time delay along the same scan-line.

For example, desiring to collect a B-mode and an Harmonic Imaging mode image, along the same scan line two ultrasound beams are projected one after the other in the region under examination each one being optimized for one of the two modes and each one of which causes a reflected beam respectively optimized for B-mode Imaging and for Harmonic Imaging. The received signals may then be processed in parallel or by multiplexing according to the above mentioned options.

It has to be considered that some Imaging modes such as Pulse Inversion, or Pulse Differentiation modes need for themselves that two or more ultrasound beams are projected along the same scan-line. In this case, depending on the further imaging modes to be combined, one of the reflected beams due to one of the said projected beams may be used or a new ultra-sound beam may be projected into the region under examination along the same scan-line.

As far the described method may lead to long acquisition times for each image. In order to shorten the imaging time, the present invention suggests to process or to generate different projecting beams for different reflected beams along each scan-line (depending on which of the above options has been chosen) for one of the two, three or more imaging or processing modes whose image data has to be displayed in a combined manner only for part of the scan-lines which form an image scanning plane or slice through the region under examination.

Considering that each image. along a predefined image scan-plane is formed by a certain number of adjacent scan-lines, it is possible. to choose any combination of number of lines and positions of the lines in the slice or scan-plane to be processed according to the two or more imaging or processing modes or only to one or less than the maximum number of processing modes provided.

For each imaging or processing mode of the at least two or more imaging or processing modes the signals of the reflected beam along a different number of scanlines is chosen among the total number of scan-lines forming a slice or scan-plane through the region under examination, the received signals due to the reflected echoes along the said chosen scan-lines is processed according to the corresponding imaging mode.

This means that assuming that a slice or scan-plane through a region to be examined is formed by a certain maximum number of scan-lines, the received signals due to the reflected beams along all or only along certain specific or selected scan-lines is processed according one of the two or more of the imaging modes provided, while the signals due to the reflected beams along selected scan-lines is processed only accordingly the other of the two or more of the imaging or processing modes provided or according to only some or all of the said processing or imaging modes provided.

Assuming for example the choice of processing the ultrasound echoes according to the B-mode and to Harmonic Imaging mode, it is possible to process the ultrasound echoes along all scan-lines forming the scan-plane or slice according to the B-mode, while only a limited number of the total number of scan-lines is processed according the Harmonic Imaging mode or by both the said modes. The above teaching may be extended also to situations where three or more processing or imaging modes are chosen, and every kind of combination or selection of scan-line may be used, also by choosing different scan-lines or partially coinciding scan-lines for each mode. The choice of the scan-lines to be processed with one of the two or more imaging modes is not limited to the number of scan-lines but also to their location in the array of adjacent scan-lines forming the scan-plane or slice.

Thus for example adjacent scan-lines may be processed only with one of the two or more processing or imaging modes.

In a different embodiment, groups of adjacent scan-lines covering one or more partial regions of the entire scan-plane or slice may be processed according to one or more different processing or imaging modes while all the scan-lines are processed according one or more other imaging or processing modes.

This feature of the method according to the present invention allows to limit the processing times, since the double triple or multiple processing according to the two, three or more of the processing or imaging modes provided can be limited only to certain regions in which the use of alternative processing modes is useful or necessary for obtaining images of the particulars searched.

It is to be stressed out the every combination of choice may be made according to.the above mentioned feature.

It is also to be stressed out that the possibility of choosing the kind and the number of processing modes that will be used to process the received signals along each scan-line allows to influence two parameters, namely: the region of the scan-plane or slice the signals received from which may be processed by one or more further processing modes, as explained above, and also the density of the scanning lines the receiving signals along which are processed according one or more further processing or imaging modes.

In a particular case where only two imaging modes are used, for a first echo signal processing mode as the so called B-mode the maximum possible scan-lines are chosen, while for the at least second echo signal processing mode a reduced number of scan-lines is chosen either by limiting the density of the scan-lines or by limiting the width of the scan-region with respect to the maximum possible width of the said scan-region or by choosing more than one limited regions distributed over the scan-plane or slice.

Using for example the ultrasound imaging technique for acquiring internal images of a human or animal body, and desiring to image a predetermined limited region of this body and the vascular flow activity. in this predetermined region under examination it is possible to process the received echo signals of all the scan-lines forming the scan-plane or slice according to the B-mode, and to limit the processing according to the processing or imaging mode optimized for detecting vascular flow only for the scan-lines which forms the part of the scan-plane coinciding with a limited zone of the said region under examination where the blood vessel are located. In this case a first B-mode image covering the entire region may be acquired and then the parameters limiting the part of the scan-plane or slice coinciding with the zone where the blood vessel are located or with the region where the vascular activity is of interest may be defined with the help of the B-mode image. The scan-lines corresponding to the said zone may then be identified and the signals of the reflected beams along this selected scan-lines may be processed according to the second imaging or processing mode.

A further improvement may consist in the fact that at the border regions of the part of the scan-plane or slice, the corresponding scan-lines are processed according to the at least further processing or imaging mode, some more scan-lines located outside of this part of the scan-plane or slice may be also processed according to the said further processing or imaging mode, the density of this lines being reduced with respect to the normal one. This means that in the border regions outside of the said part of the scan-plane the signals relating to reflected beams along only a reduced number of scan-lines are processed according to the at least further processing or imaging modes, the said scan-lines being chosen not adjacent one to the other but separated by other scan-lines which are processed only according to the first processing or imaging mode.

Thus the image obtained according to the said at least further processing mode will have a lower definition at the border regions allowing to enlarge the field of view without reducing too much the overall imaging time.

This feature of the method according to the present invention is particularly useful considering the use as one of the processing modes of the Harmonic Imaging modes combined with contrast media. Contrast media are injected in the region under examination and provides enhancing effects for imaging vascular or similar physiological flows and/or stationary contrast media bubbles in the region under examination. Contrast media have a limited lasting time within the region of interest and their concentration due to the transport of the contrast media microbubbles by the flow slowly increases after injection and then again decreases. Thus long lasting imaging methods have the drawback that the image may be acquired when the contrast media concentration is too low in the region under examination. In this case there will be no sufficient time for repeating the image acquisition again and there might be the necessity of undesirable repeated contrast media injections in the region under examination. Too long lasting imaging methods further may fail with contrast media because the user may orient wrongly the probe imaging a completely wrong region or only partially the region of interest with the need also in this case of undesirable repeated injections of contrast media.

Reducing the time for acquiring an image will drastically reduce the need of repeated injection of contrast media in case of failure of the synchronisation of the acquisition of the image with the perfusion of contrast media in the region under examination or of a wrong orientation of the probe. After having displayed the first image there is sufficient time left for further correct image acquisitions. In case that no such failures occur more time is left for acquiring images of the interesting regions and an higher frame rate may be achieved.

It is important to understand that although the above mentioned method is described only with respect to the provision of the processing of the received signals corresponding to the reflected beams according two or more processing or imaging modes, the principle mentioned above may be also applied to the projection of multiple beams along the same scan-line. In this case according to the present invention the choice is provided to select for each single scan-line if along this line there must be projected only one beam or more subsequent beams each optimised for one or a part of the processing or imaging modes.

According to an further improvement of the method of the present invention which may be provided alone or in combination with the other steps or features, a shortening of the image acquisition may be achieved by means of the fact that the received echo signals of at least one or more or of at least part or of all the scan-lines are processed at least partly according to only one of the two processing modes and partly according to the other processing mode or according to a combination of the two processing modes by processing the time dependent signal of the reflected beam along the said scan-line with only one of the said two processing mode or with both modes for different parts corresponding to different or at least overlapping time periods of the duration of the reflected signal, which time periods corresponds to information reflected by tissues at different depth in the direction of the scan-line along which the projected beam has been focussed.

The reduction of the information that is to be processed by means of two or more processing modes deriving form the limitation of the part of the signal according to time automatically reduces the overall duration of imaging. The line limitation may be chosen in such a way that the reflected signals from a certain depth range in the region under examination are chosen. This may be achieved in a similar way as to the choice of the limited number of scan-lines which signals have to be processed according to the further processing mode, by acquiring and displaying a complete B-mode image of the region and than by defining the time interval of the received signals to be processed with the further processing or imaging modes by means of the B-mode image of the entire region.

Obviously instead of a B-mode image, the entire image of the region under examination may be constructed by means of other processing or imaging modes.

Combining this feature of the method according to the invention, i.e. the limitation of differential and/or parallel multiprocessing of the signals by defining time limited parts of the signals, with the limitation of differential and/or parallel multiprocessing of the signals by means of limitation of the number and/or location of the scan-lines will lead to a further reduction of the total imaging times.

It is further to be stressed out that the two above mentioned teachings for limiting the overall duration of imaging may be provided either alone or in a combination with the method steps for displaying in a combined manner the image data obtained by two or more different imaging modes.

Another feature of the present invention which can be provided separately or in combination with one or more of the above mentioned features regards method steps for measuring the perfusion of a contrast medium in a region under examination.

The measurement of perfusion curves by mean of ultrasound imaging may be obtained by injecting a contrast medium in the region under examination and by emitting particular projected beams for exciting a beam reflection which is sensitive to the vascular flows as for example according to the Harmonic Imaging mode or other kind of imaging modes. The projected beam may have a reduced or limited mechanical index at a level lower than the mechanical index needed to destroy or burst the contrast media micro bubbles. Alternatively the mechanical index of the projected beams may be sufficiently high to destroy a certain part of the microbubbles.

The evolution of contrast media enhancement or perfusion as a function of time in the region under examination is then detected by firing successive ultrasound projected beams covering the region under examination of the tissue imaging region. The time between injection of contrast media and instant at which firing of the ultrasound projection beam occurred or the time passed between the firing of each subsequent projection of a beam along the same line is then measured. The time measured being univocally correlated to each projection beam and to the corresponding reflected echo signal and the image data are stored in a image memory according to a image sequence based on the measured time at which each image has been acquired. Each time correlated image obtained and stored is then displayed in a film like succession.

For instance, in the case of liver scanning, the above mentioned method steps allow to make comparison between venous or arterial perfusion curves in a region under examination and a sample or samples of typical venous or arterial perfusion curves of other tissues which may show a particular pathology or which does not suffer of any pathology. The difference may be enhanced on the display by displaying in combined manner and with a predetermined color the differences or the two perfusion behaviors according one or more of the previous method steps for combined display of image data having different origin or obtained by different processing or imaging modes.

Similarly also a comparison between arterial and venous perfusion of contrast agents in the same tissue or region under examination may be made. This may help in enhancing features for better signal the presence of certain pathologies. In this case, in a tissue imaging region comprising arterial and venous blood vessels an image is displayed obtained by combining information processed according to B-Mode imaging of the tissue and information processed according to the second processing mode of the. arterial blood flow. This image is compared to an image representing a combination of information obtained by B-Mode imaging of the tissue and information obtained by the second processing mode of the venous blood flow. A time correlated image sequence may be acquired for both arterial and venous flows and the two image sequences may be compared one with the other and/or with typical sequences related to arterial and/or venous flow obtained by acquisition of images of a tissue showing a particular pathology or not showing any pathology at all.

A further possibility of comparison may take into consideration the comparison of contrast media perfusion behavior in the arteries and/or in the veins in a region under examination with the behavior of contrast media perfusion in particular samples tissue kinds.

According to yet another variant of the present method, successive groups of projected beams each one focussed on one of more scan-lines covering a certain imaging region are fired for obtaining successive image information of a certain slice of the imaging region being each group of projected beams covering the selected image region preceded by a high energy projected beam with a mechanical index suitable for completely or partially destroying contrast media present in the said imaging region and by executing the firing of each group of projected beams with different step like longer lasting time periods from the firing of the preceding group of projected beams in order to acquire so called-perfusion curves.

According to a first embodiment an automatic time basis is provided for automatically determining the moments of firing each successive projected beam or group of projected beams covering a certain area of interest. The firing of each ultrasound beam or of each group of ultrasound beams is executed in an automatic way.

According to a second embodiment which may be provided in combination with the first one as a second operative option, the firing of each group is executed manually.

As a further improvement of the above mentioned method for measurements of perfusion curves and for comparing the venous and/or arterial perfusion in the region under examination with samples of typical perfusion curves in tissues showing a specific pathology or not showing any pathology, the method provides the steps of displaying virtual images of the flow superimposed or combined with the B-mode image of the region under examination.

This may be achieved by extracting the image data for each image of the sequence of images from the known image or perfusion data of the sample tissues showing a particular pathology or not showing any pathology and by using this sample image data as the image data of the second imaging mode, i.e. the imaging mode selected for imaging the venous or arterial flow in the region under examination, in order to display this sample image data in a colored manner and combined or superimposed on the acquired B-mode images of the region under examination. A virtual sequence of images of the region is then reconstructed virtually showing the sequence of images of the region under examination as if the particular pathology would be present in that region and/or if no pathology at all would be present in that region. This virtual sequence may be displayed in a window adjacent to a further window for displaying the combined image data processed according to the B-mode and to a further processing or imaging mode particularly suitable for imaging venous or arterial flow.

In this case it is also possible to use different colors for displaying the image data processed according to the second processing or imaging mode combined with the B-mode image and the data retrieved from the stored sample images combined with the B-mode image acquired. So the user may better discriminate the probability that a pathology may exist in the region in examination.

Eventually three windows of combined image data may be displayed at the same time and adjacent to one another each window corresponding respectively to the combined image data from the two image data set obtained by the at least two imaging modes from the echo signals reflected by the region under examination, the combined image data of one image data set obtained by one of the imaging modes from the echo signals and of the image data set obtained by the sample tissues showing a particular pathology and to the combined image data of one image data set obtained by one of the imaging modes from the echo signals and of the image data set obtained by the sample tissues not showing any pathology at all. In such a way a direct visual comparison may help the user in recognizing the presence of potential pathologies.

The invention relates also to a device for ultrasound imaging according to one or more of the above mentioned method steps and showing such features as an ultrasound probe with a linear or two-dimensional array, a transmission beamformer, a receiver beamformer, at least two different processing channels for extracting/reconstructing displayable image information, means for combining the image information, and means for displaying the image information.

SUMMARY OF THE INVENTION

A method for ultrasound imaging of tissues located in a tissue image region according to one embodiment of the present invention comprises the steps of projecting at least one ultrasound beam into the tissue image region, receiving ultrasound reflections, and transducing the reflections into electric echo signals, processing the echo signals according to at least two different modes, one of the processing modes being an imaging mode and the other processing mode being a different echo processing mode for imaging particular tissues, displaying the images obtained in an interleaved or combined, such as superimposed, manner on the same screen, displaying the image obtained from the first mode with a gray-scale and displaying the image obtained by the second mode in a colored manner by choosing a color adapted to the optimum physiological capability of human eyes to discriminate the information displayed by the color level scale.

One object of the present invention is to provide an improved method for ultrasound imaging of tissues located in a tissue image region.

Related objects and advantages of the present invention will be apparent from the following description.

DESCRIPTION OF THE PREFERRED EMBODIMENT

Figure 1:
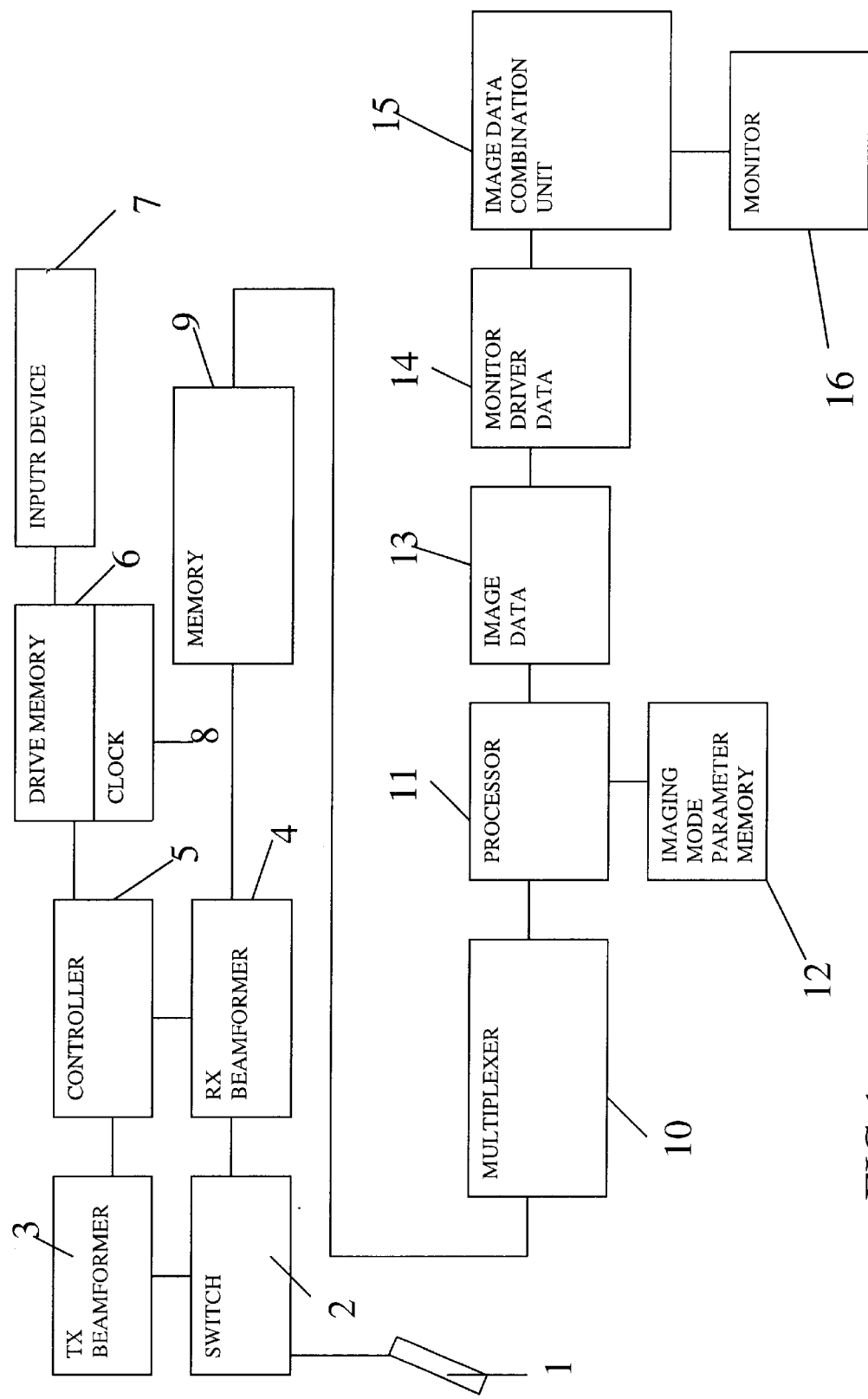
FIG. 1 is a schematic block diagram of a first embodiment of an ultrasound imaging device according to the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

According to FIG. 1, an ultrasound imaging device, such an ecographic device comprises a probe 1 which is provided with electro-acoustic transducers for transforming electric excitation signals in ultrasound impulses and vice-versa. Many kind of probes are well known in the art and comprise linear or two-dimensional arrays of such transducers. Each projected beam emitted by the probe along a certain scan-line through a region under examination is formed by the sum of the acoustic impulses generated by all or of only a selected part of the electro-acoustic transducers. The transducers are excited by electric excitation signals which are fed to them according to a predefined order and scaled in time in such a way to generate an acoustic ultrasound beam focussed on a chosen scan-line. The image of a slice or cross section of the region under examination is formed by the reflected beams according to a linear array of adjacent scan-lines distributed along the scan-plane or slice containing the said scan-lines. The reflected acoustic signals are received by the transducers and transformed in electric signals from which the reflected beams are reconstructed by using essentially the inverse focussing law by which the projected beams are generated. The projected beams propagate with a certain. velocity in the region under examination and time is a measure of the depth of penetration of the projected beams through the region under examination. Thus reconstruction of a reflected beam due to a certain projected beam has to be made considering the time of detection of the acoustic impulses and the timetable of excitation to the emission of the acoustic impulses by the single transducers.

Figure 2:
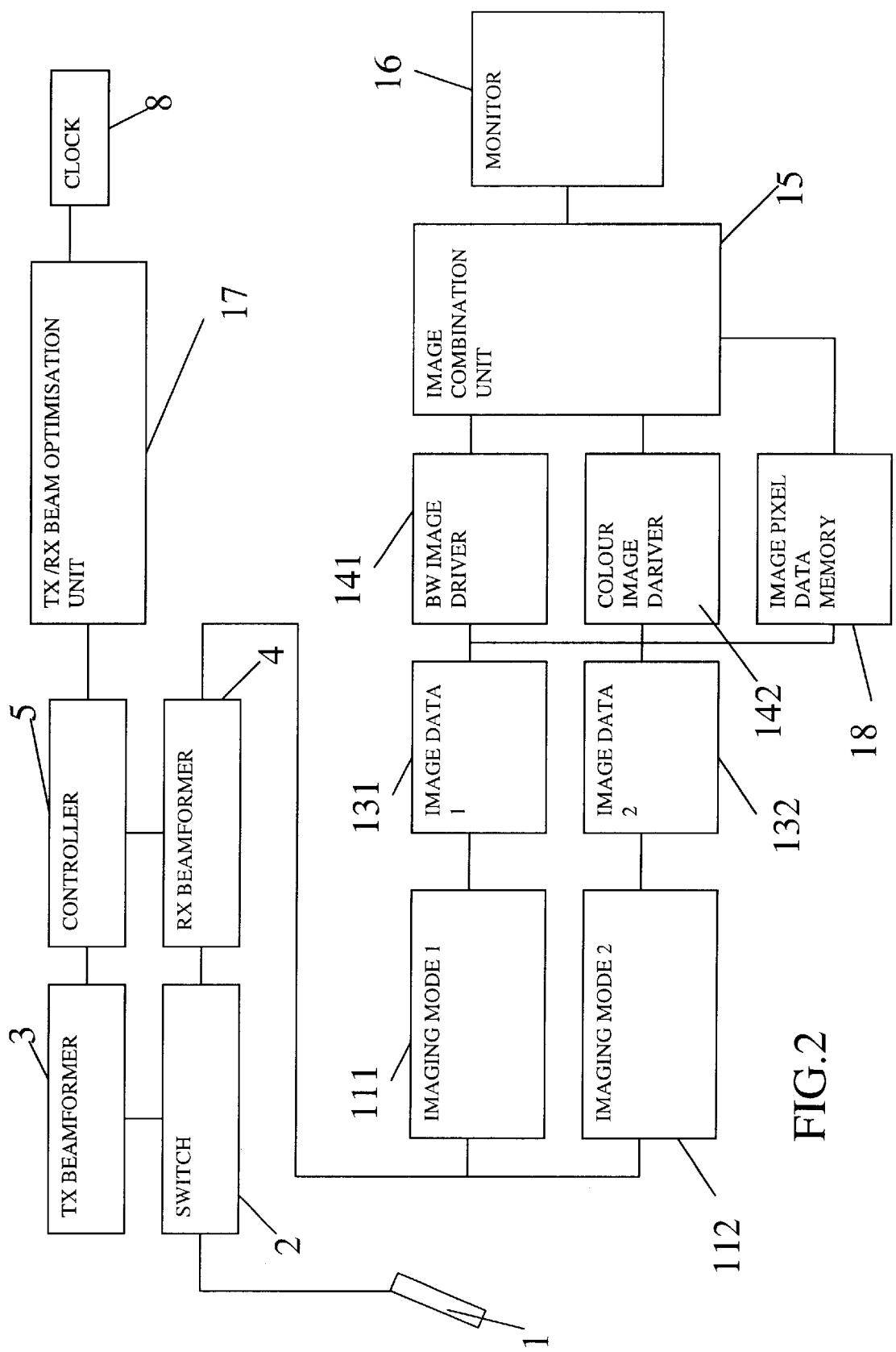
FIG. 2 is a schematic block diagram of a second embodiment of an ultrasound imaging device according to the present invention.
Figure 3:
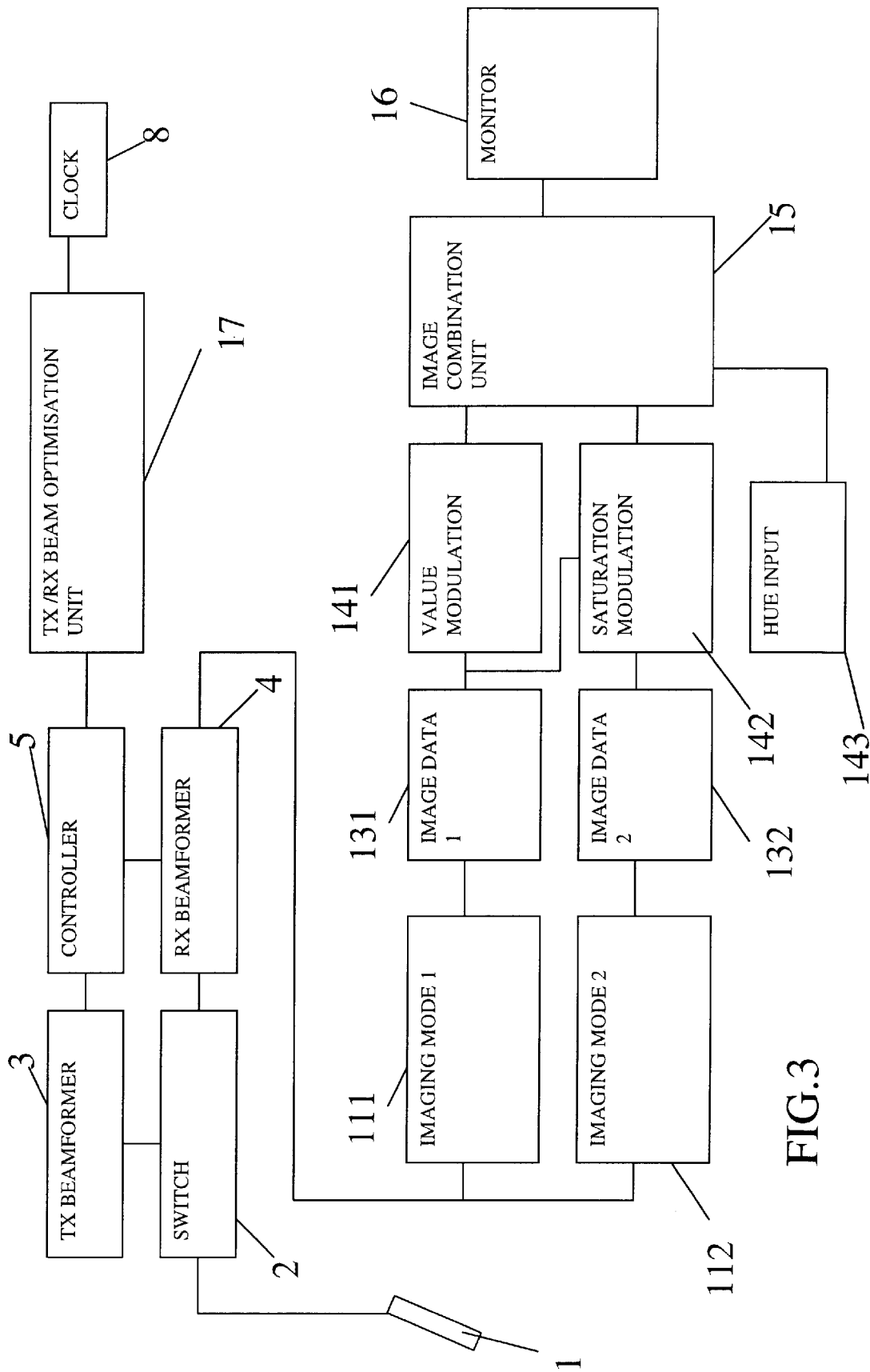
FIG. 3 is a schematic block diagram of a third embodiment of an ultrasound imaging device according to the present invention.

Since in the examples illustrated in FIGS. 1 to 3 the probe is destined for emission of the projected beams and for the receipt of the correlated reflected beams a switch 2 is used which connects alternatively and in an appropriate way the transducers of the probe 1 to a transmission beamformer unit 3 and to a reception beamformer 4. This units are driven by a controller 5 in which the different beamforming rules and projected beams parameters as well as the different reconstruction rules for obtaining the reflected beams are stored. This is indicated by the unit 6 defined as driver memory of the controller unit 5. A clock 8 gives the time basis for applying the transmission and receipt beamforming rules and for correctly driving the switch. Input devices 8 are provided for the input of the beams parameter and for the beamforming rules.

It is to be noticed that the actual device may be provided also in combination with a probe having different transducers for the projected and for the reflected beams and that the method steps according to the invention may be applied also to this kind of probes.

According to the example of FIG. 1, the reflected beams are processed by two different processing or imaging modes for obtaining useful image data in a format which may be used for drive a monitor or other kind of visualization device.

A multiplexer 10 which is synchronized with the signals due to the reflected beams along the different scan-lines controls the input to a processing unit 11 of the said signals corresponding to one or more reflected beams along a scan-line. In a synchronized manner with the multiplexer the processing unit 11 transforms the received signals in image data 13 according to at least two different processing or imaging modes. The received signals related to each scan-line are stored previously in a memory 9 for allowing the subsequent processing according to the at least two imaging modes. The parameter and processing protocols according to the at least two processing modes are stored in a dedicate memory 12 from which they are called and by the processing unit 11. Image data 13 furnished by the processing unit 11 are transformed in monitor driver data in a unit 14 and then the image data according to the at least two imaging modes are combined together in a image data combination unit 15. The combined image data are then used to drive a monitor 16 in order to display the image acquired by the ultrasound beam reflection. It is to be stressed out that the combination unit 15 and thus the combination step may be executed at an earlier stage as for example prior to transform the image data 13 in monitor driver data 14.

Since many kind of imaging or processing modes are well known and widely used any kind of processing or imaging mode may be used as the at least two different processing or imaging modes, particularly the so called B-mode, Harmonic imaging mode, Pulse Combination or Differentiation modes, such as for example Pulse Inversion mode, Doppler and Power Doppler modes, Color or power color modes and with or without the combined injection on the region under examination of ultrasound reflection enhancing media such as contrast media, or the like. This appears clearly from the above description, since no reference to a particular imaging mode has to be made in order to carry out the principal steps of the invention and the units needed in the device may be defined in a general manner.

Any kind of combination of the image data according to the at least two imaging modes may be used. The image data, i.e. the images resulting from each of the at least two different imaging modes may be displayed with different color ranges, one in black and white and the other in a predefined color range, one image near the other or both images superimposed one on the other or alternating each other on the screen.

Since normally B-mode images are sufficient for panoramic views of the region under examination and since other imaging modes are used for detecting and imaging particular tissue structures or other kind of objects as for example vascular or other physiologic flows, it is a preferred embodiment to display the Bmode image or the panoramic image of the region under examination obtained by another kind of imaging mode in black and white or in a gray scale image, while the image obtained by the at least second imaging mode is displayed in color. In order to facilitate recognition of the image according to the at least second imaging mode and the desired information obtained by this at least second imaging mode the invention a particular color range may be chosen for this image due to the second imaging mode. According to a first feature the color range is chosen among the color where the human eye has the best response of recognition. Among this color ranges the best one has be discovered to be the color range corresponding to the wavelengths going from green to yellow.

An advantage of the device according to FIG. 1, is the fact that hardware costs are limited since only one rocessing channel is used for the at least .two different processing modes.

The advantage of the combined display of ecographic images obtained by at least two different imaging modes consists in the fact that it is possible to display at the same time more precise information. The panoramic vision of the region under examination and the superimposed colored display of image data obtained by means of imaging modes which reveals details for example of the condition of the vascular circulation or are more sensible to tissues executing limited micromovements, enables to evaluate the position or location of the vascular flows or of other flows or of a particular tissue region characterized by intense micromovements and the parameters of the said flows and or micromovements. This is helpful for diagnostic evaluation of the images and or for monitoring therapeutic or invasive intervention by means of needles, or other needle like devices.

Particularly in combination with the injection in the region under examination of ultrasound response enhancing media such as for example the so called contrast media, the combined display of a panoramic view as a B-mode image and of the image obtained by an imaging mode sensitive to the said response enhancing media or contrast agents such as for example the so called Harmonic Imaging mode, the device and method according to the invention allows to recognize very fast if the probe is correctly oriented relatively to the region under examination in order to aim to the limited region where the response enhancing media or the so called contrast agents has to be revealed. This allows to immediately orrect the orientation of the probe and .in such a rapid manner to obviate to the need of a repeated injection of the response enhancing media or of the contrast agents. This media and the contrast agents arrives at the region under examination with a delay with respect to the moment of injection and rests with a sufficient concentration within the region under examination for a certain limited time period. Thus if the probe is incorrectly oriented and does not aim to the correct object to be examined and if the service person does not have any information on which he can relate in order to correct the orientation of the probe, the different attempt to correct this orientation may not lead to the correct orientation within the time period of presence of the response enhancing media or of the contrast media within the region under examination.

It is possible to carry out the above mentioned imaging steps by means of the device of FIG. 1 which provides multiplexed input to a common processing channel which is set alternatively to operate according to one of the at least two imaging modes due to the fact that it takes some time to generate the focussed scanning beams and to reconstruct the related reflected beams and further due to the memory 9. Furthermore it is to be considered that the processing may request relative long times depending on the kind of imaging modes chosen.

The structure of the device of FIG. 1 allows to load in the memory 12 of the processing unit 11 the algorithm or programs and the parameters of an indefinite number of processing or imaging modes and to choose at any time the processing modes which has to be used for treating the received signals. So three, four or more processing modes may be used to successively evaluate the received signals in order to obtain a corresponding number of image data which may be displayed superimposed or partly superimposed or side by side or in overlapped layer which may be chosen by recalling each layer on the monitor.

Particular programs in combination with selection devices such as for example knobs or levers or a mouse may be provided for selecting the displayed layer and choosing the different possible combined display of all or part of the images obtained by the different modes.

FIG. 2 shows a variant of the device according to FIG. 1 in which there are two parallel channels for processing the received signals according to at least two different imaging modes. In this case, the embodiment shown is limited to two channels for processing the received signals according to two imaging modes. This embodiment must not be considered as limiting the device to only two processing channels but there might be also three or more processing channels each one optimized for the processing of the received signals according to a different imaging mode.

In FIG. 2 identical units as the one shown in FIG. 1 as been indicated with the same reference .numbers as in FIG. 1.

As a first difference this embodiment shows a TX/RX beam optimization unit 17 which drives the controller of the beamformers for the projected and the reflected ultrasound beams. This unit allows to set the beamformers 3 and 4 in an optimized way for one of the two or more processing modes of the received signals and/or for the projected beams in order to optimize their parameters such as frequency, resolution (scan line density), mechanical index or beam intensity in relation to the different imaging or processing modes implemented in the device. For example it is possible to fire along the same scan-line different subsequent beams which have an optimized frequency and/or an optimized intensity or mechanical index and/or an optimized focalization for each one of the two or more processing modes. This leads to subsequent reflected beams along the same scan-line which are already at least partially optimized for the different processing or imaging modes.

It is to be stressed out that this construction is not to be considered limited to the embodiment of FIG. 2 but that it can be provided also in combination with the embodiment of FIG. 1.

Each of the two processing channels has respectively a processing unit 111, 112 for processing the received signals according to a first and to a second imaging mode at the same time. This is done irrespectively if only one beam is projected into the region under examination for each scan-line or if two subsequent beams each optimized for one of the two processing or imaging modes are fired along the same scan-lines. Image data 131 and 132 furnished by the two parallel processing units 111 and 112 are then used. for obtaining a black and white or a gray scale image driver 141 and a color image driver 142 for the monitor 16. This data 141 and 142 are fed to a combination unit 15 which displays on the monitor the images relating to the two channels in a desired way as for example in frames placed side by side or superimposed.

Also in this embodiment as in the example of FIG. 1, all kinds of combinations protocols of the images are possible. The same is valid for the stage at which in the processing channels the signals or data are combined together. The combination may be executed at the end of the processing channels or at the image data stage or in any other point of the processing channels.

According to a further feature of the example of FIG. 2, an image data memory 18 is provided for storing images of the same slice or scan-plane taken at different times. This images may be used for being displayed in a sequence like a short film or for being evaluated numerically for obtaining visual and numerical information about time dependent events taking place in the region under examination. The clock 8 provides for the time basis which is used for the time dependent acquierement of the images forming the sequence.

This option may be used in combination with at least one imaging mode such as for example the Harmonic Imaging mode or Pulse Inversion mode and in combination with injection of contrast agents in the region under examination to carry out perfusion measurements of the contrast agents which give a measure of the vascular flow conditions. In this case the perfusion can be measured relating to the venous circulation the visual sequence memorized and/or the numeric information extracted by the imagines forming the sequence may be compared to visual sequences of images of a sample tissue and or to numeric information extracted therefrom. The sample tissue may be a sample tissue of another region of the same body or of another body or obtained by a theoretically constructed sample. The sample tissue may be a tissue in which particular conditions may or may not exist. In the case of a diagnostic use of this method the sample tissue may be a perfectly sane tissue or a tissue showing a conclamated and identified pathology such as cancer formations or other.

According to a further option, sequences of images may be acquired of the arterial flow conditions and this sequences may be treated in an analogous way as explained above for the images of the venous circulation in order to carry out a perfusion measurement of the contrast agents in the arterial circulation and compare the results with the measurements obtained from a sample tissue.

The memory 18 allows also to compare perfusion measurements of the venous circulation with the one of the arterial circulation.

Yet another option which may be provided consists in the possibility of reconstructing the flow conditions of the sample in the image sequence of the region under examination. This option may be carried out in the best way by combining a B-mode panoramic image sequence processed by one of the processing channel with a sequence of images processed according to the Harmonic imaging mode or other suitable imaging modes. In this case each image of the sequence according to the B-mode being displayed in a gray scale is combined with the corresponding image according to the Harmonic imaging mode or to the other mode selected which is displayed in color. From the data obtained by the sample tissue a visual model, namely a theoretical image of the conditions existing in the model may be reconstructed for the image sequence of the region under examination and superimposed to the B-mode image sequence in an identical way as the images of the arterial or vascular circulation images directly acquired from the region under examination. In this way a model of the probable images obtained by an hipotetic region under examination in which the same conditions as in the sample tissue are present may be compared with the images obtained by the direct acquisition of the images from the region under examination. The comparison may be made visually by displaying both sequences in different areas of the monitor side by side or by displaying both combined images superimposed one on the other and giving different colors to the image data relating to the vascular or arterial flow and due to direct image acquisition and reconstruction from the known sample.

Perfusion measurements or imaging of the conditions of the vascular circulation may be acquired by using mechanical index for the projected beams that causes the contrast agent microbubbles destruction. In this case the sequence of images is taken after having destroyed the contrast agent microbubbles or by applying imaging techniques which use mechanical index of the projected beams that avoid or limit the contrast agent microbubble destruction.

FIG. 3 shows a further example of a device according to the invention. In this example a particular way of combining the image data obtained by two different processing or imaging modes from the received signals is shown. It is to be noted that this example may be provided in combination of the other features of the preceding examples and vice versa. So it is possible to use the particular way of combining the image data shown in FIG. 3 also in combination with a multiplexed singular processing channel or with the particular arrangement of FIG. 2 that allows acquisitions of image sequences for performing perfusion measurements.

In the present example the image data obtained by the two processing channels treating the signals according to two different imaging modes are used to drive different image parameters. The image on the monitor screen may be constructed according a so called HSV protocol, i.e. Hue, Saturation and Value. In this case the parameter Hue defines the color wavelength range. The Saturation defines the colour amount and the Value defines the intensity or luminosity of the pixels in a black and white or gray scale image.

In order to achieve a better combined image, where the color image data obtained by one of the two imaging modes, particularly by processing the received signals according to an Harmonic Imaging mode or a Pulse Inversion mode or other modes, is modulated relatively to its transparency of the superimposed colored image on a black and white or color image which depicts the image data processed according to the other imaging mode, particularly a B-mode the image data relating to the B-mode modulates the value parameter, while the image data obtained by the Harmonic Imaging mode or the Pulse inversion mode modulates the saturation. The Hue parameter is defined by default in a particular wavelength range.

In the case of processing the image data according to three different imaging or processing modes this imgage data may be combined by further modulating the Hue ccording to the image data of the third imaging or processing mode. Alternatively two or more separate but fixed wavelength ranges may be defined and the Hue will be set according to one of these different wavelength intervals on the basis of the image data obtained by the third imaging or processing mode.

The third processing mode image data may also used for modulating the saturation in a different wavelength interval for the hue then for the second imaging mode. Instead of a HSV protocol also a HLS or other similar protocol may be used.

According to a preferred embodiment the image data of the second imaging mode, particularly an Harmonic Imaging mode or a Pulse inversion mode are combined with the image data of the first imaging mode, particularly a B-mode according to the following algorithm:

alpha*first-mode+(1-alfa)*second-mode.

Preferably the first imaging mode is a B-mode and the second imaging mode is whichever imaging mode is chosen, particularly a Harmonic imaging mode.

This algorithm gives the best results in combining the black and white or gray scale image obtained by the first imaging mode with the color image obtained by the second imaging mode generating more or less transparence of the color or more or less presence of the color in the wavelength set by the Hue, depending on the image data according to the said second imaging mode.

Obviously the algorithm disclosed above is a preferred example of many different possible combination algorithm and the present invention is not to intend limited to the said one.

FIGS. 4 to 10 show some examples of imaging methods that may be carried out with the help of the above decribed devices. Particularly this methods aim to reduce the image acquisition duration from the moment of the projection of the beams to the moment at which the image has been reconstructed and displayed.

Although for simplicity the only two different images modes considered in this examples are the so called B-mode and particularly the Harmonic Imaging mode, the examples must not be considered limited to the use of only this two modes but depending on the needs any kind of mode may be Used. In the same way the examples although considering only two different imaging or processing modes must not be considered as being limited to only two modes but more than two modes may be provided.

Figure 4:
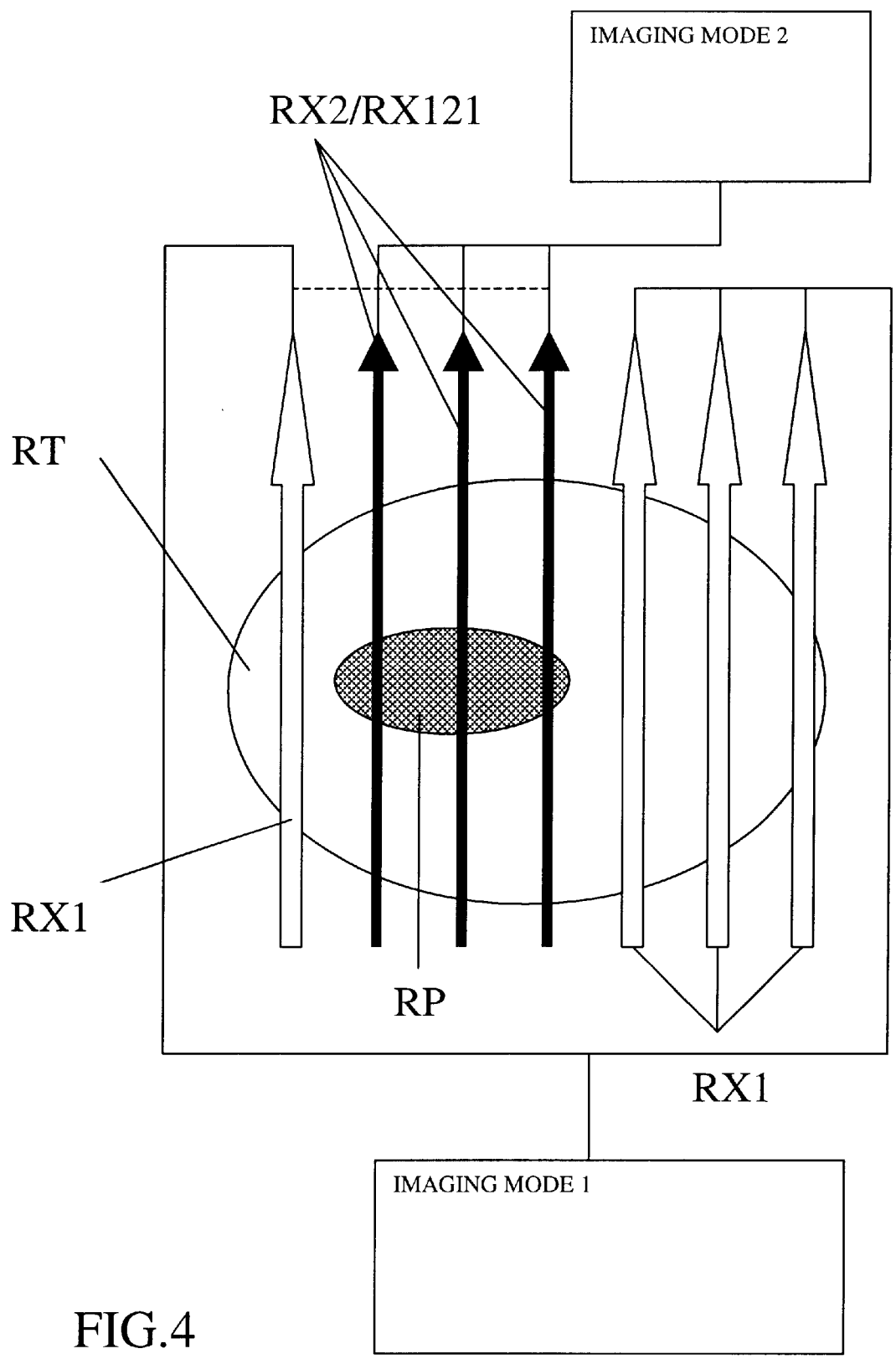
FIG. 4 is a diagram showing a first method of processing the reflected beams with two processing or imaging modes by limiting the processing of the second imaging mode only to selected reflected beams by a limited region within the region under examination.

FIG. 4 shows a first way to shorten imaging duration by limiting the processing of the received signals according to the second imaging mode to the reflected beams RX2 along scan-lines which passes through a limited or partial zone RP of the entire slice of the region under examination RT. The first imaging mode, particularly a B-mode may be used to process the signals of the reflected beams along all the scan-lines in the scan-plane or slice. As an alternative the processing of the received signals according to the B-mode may be limited to all scan-lines which will not cross the limited or partial zone RP where the reflected beams are treated according to second imaging or processing mode.

The dotted line wants to illustrate this two options.

Figure 5:
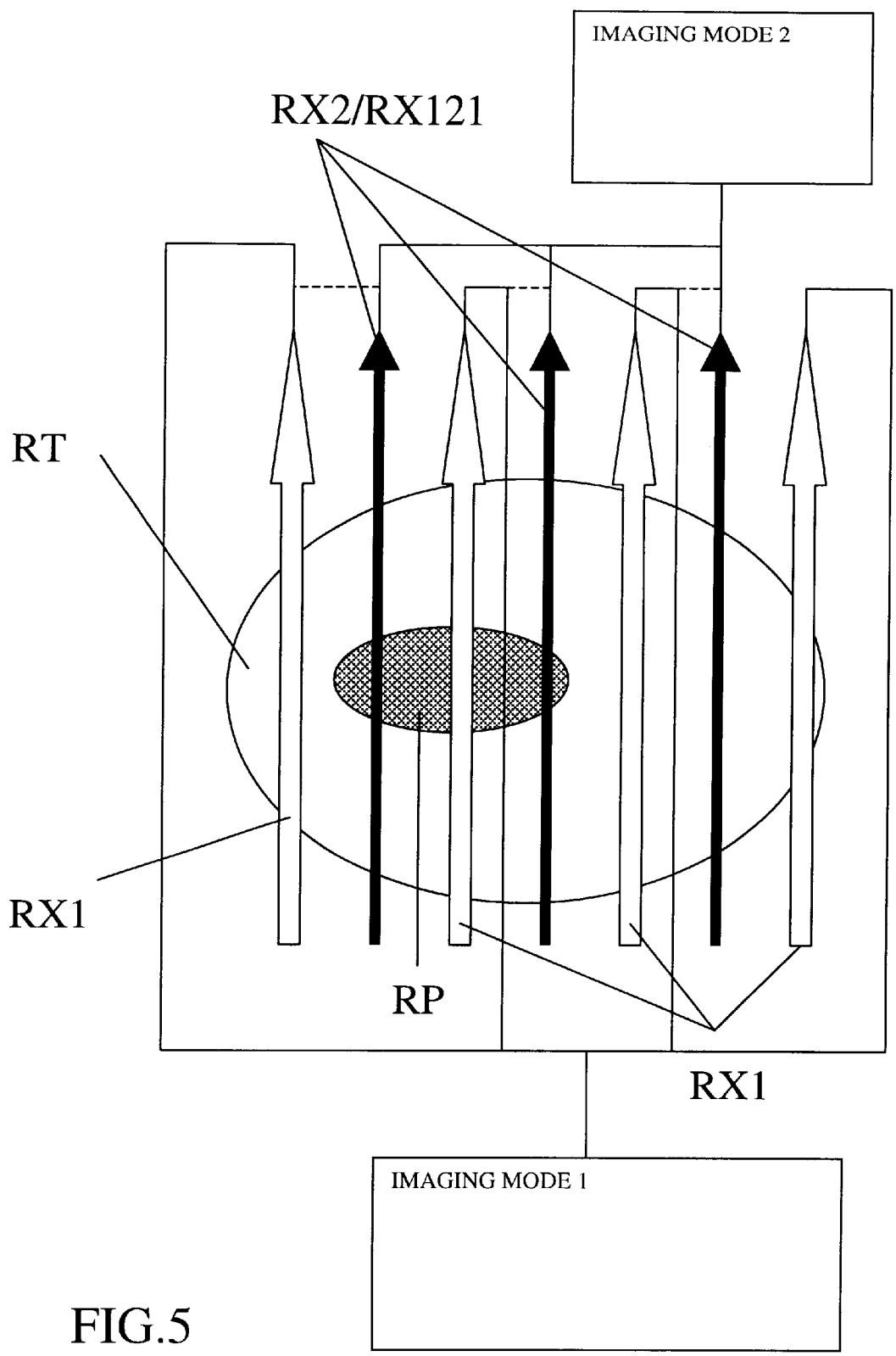
FIG. 5 is a diagram illustrating an alternative method of processing the reflected beams according to two processing or imaging modes.

FIG. 5 shows a different way of selectively limiting the processing to only one imaging mode of the two provided to certain scan-lines. In this case the received signals of the reflected beam along the scan-lines separated by one further scan-line are processed according o the second imaging mode. While the received signals of the reflected beams along each of the scan-lines or only of the remaining scan-lines are processed according to the first processing mode, particularly a B-mode.

Also in this case the dotted lines try to depict these options.

Figure 6:
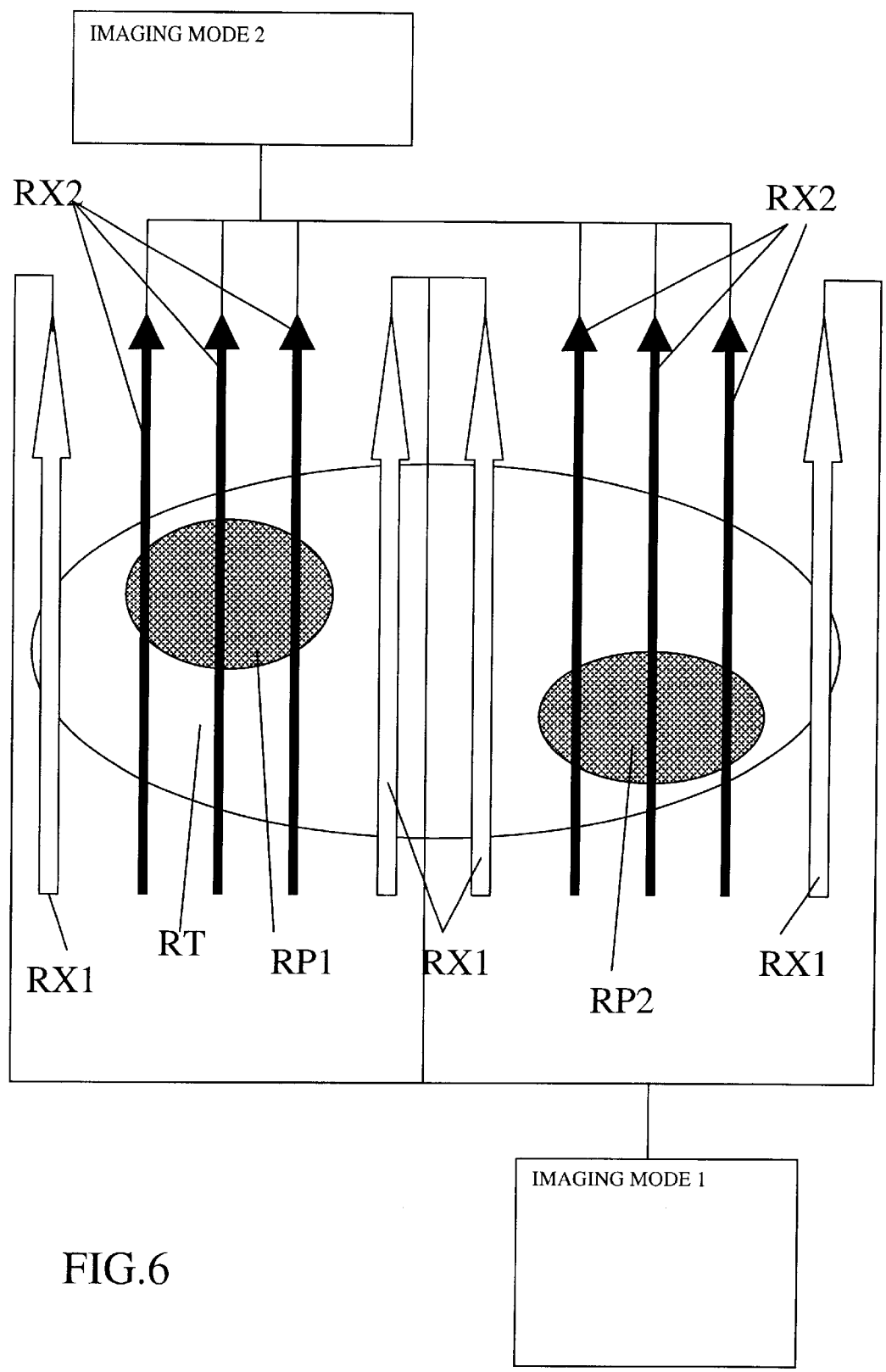
FIG. 6 is a diagram showing an improvement of the method according to FIG. 4.

FIG. 6 shows an analogous case to FIG. 4 where twopartial zones or limited zones RP1 and RP2 exists in the region under examination RT. In this case the two groups of scan-lines crossing these zones RP1 and RP2 may be processed according also to the second imaging mode or only according to this second imaging mode being the two options described in relation to FIG. 4 valid also in this case.

Figure 7:
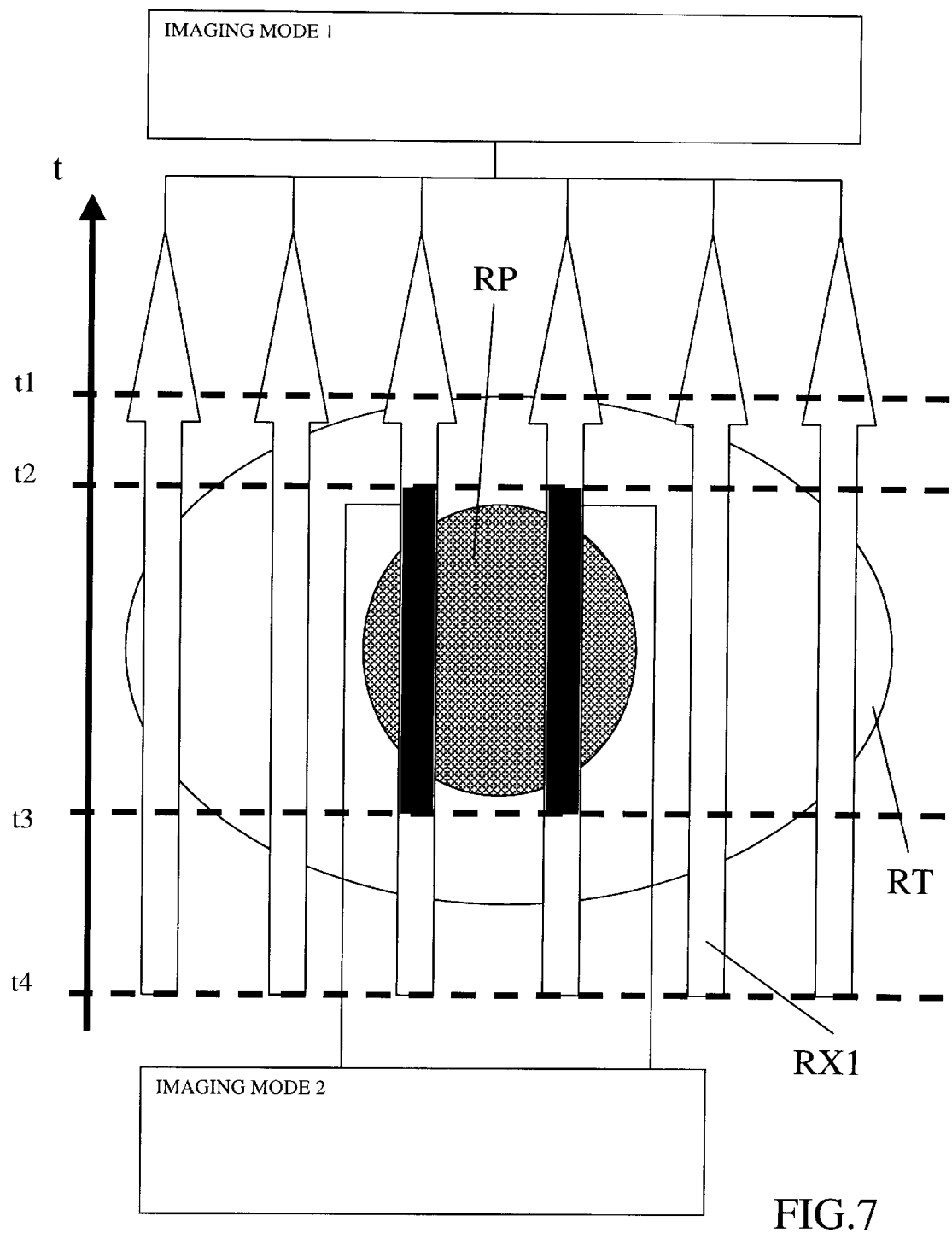
FIG. 7 is a diagram illustrating another method of processing the reflected beams according to two different processing or imaging modes in combination with the method according to FIG. 4 and which method provides the processing according to the second imaging mode only of a part of the temporal total duration of selected reflected beams by a limited region of the region under examination.

FIG. 7 shows a further way of processing received signals of reflected echoes by two different imaging or processing modes. This further way may be provided separately or in combination to the ones disclosed with reference to the preceding FIGS. 4 to 6.

In this case the limitation of the processing of the received signals of reflected echoes along selected scan-lines by means of also or alternatively a second imaging mode is made by selecting not only particular scan-lines, as the scan-lines crossing limited or particular zones RP of the region under examination RT but also by limiting the processing according to the second imaging or processing mode to only a part of the total duration of the received signal along the said scan-lines. The time interval defining the selected part of the received signal along a selected scan-line being defined on the corresponding penetration depth of the beam so to consider only the part of the beam which crosses he limited or partial zone RP. In this case the total uration of the received signals identified by RX1 and defined by the time interval t1,t4 is processed according to the first imaging or processing mode as for example a B-mode while the part of the signal corresponding to the time interval t2,t3 corresponding to the part of the beam crossing the partial or limited zone RP is processed also according the second processing or imaging mode.

Obviously this technique may be provided in combination with any of the features disclosed with reference to the preceding FIGS. 4 to 6. So for example the part of the received signal according to the time interval t2,t3 may be processed only according to the second imaging mode. Also more than one partial or limited zone RP may be considered if present in the region under examination. A different distribution of the scan lines is considered for treating the corresponding received signals according to second imaging mode.

Figure 9:
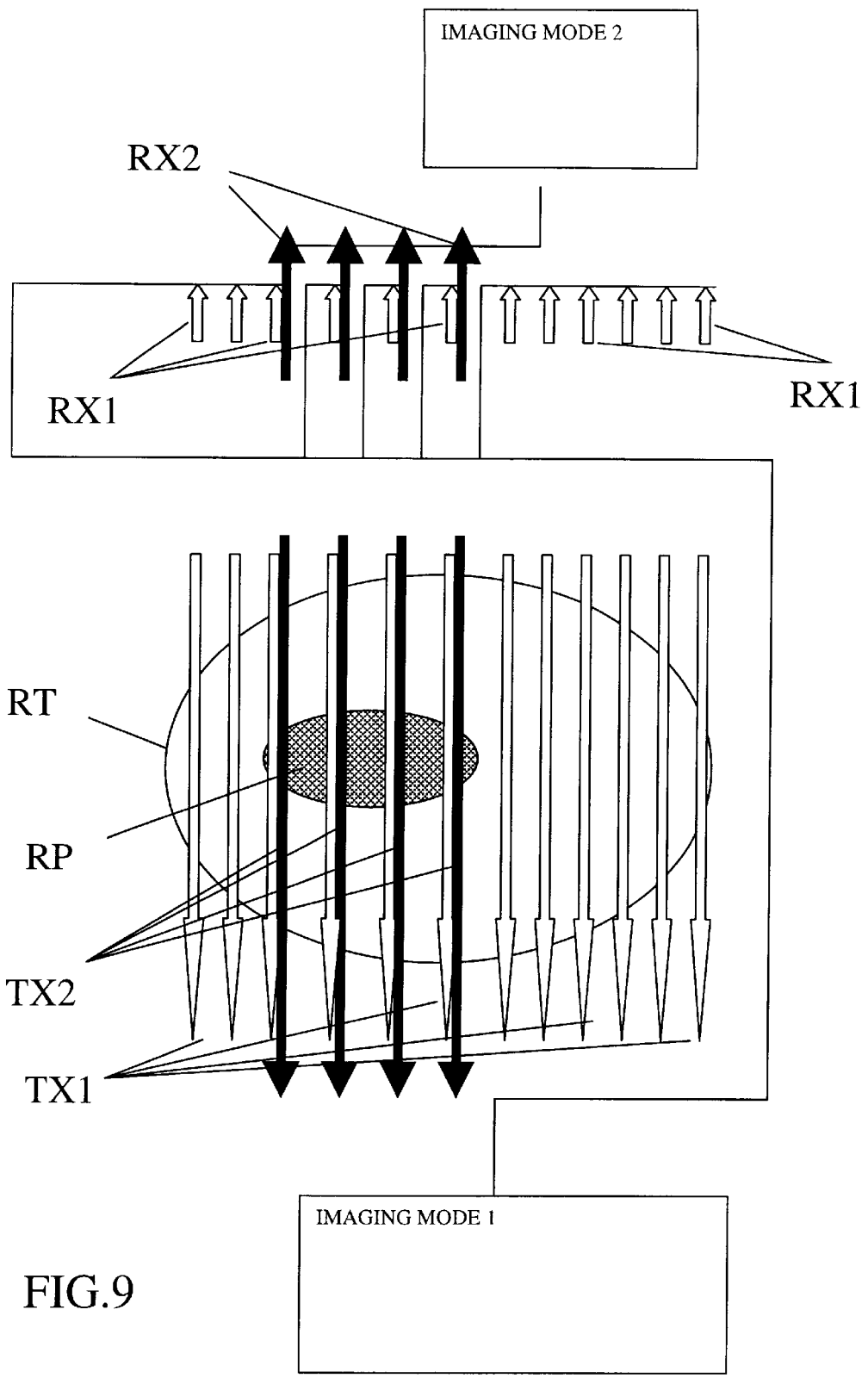
FIG. 9 is a diagram showing an alternative embodiment of the method according to FIG. 8, in which for selected scan-lines two subsequent beams are fired across the region of examination, each one of the said two beams being optimized for one of the two imaging modes.
Figure 10:
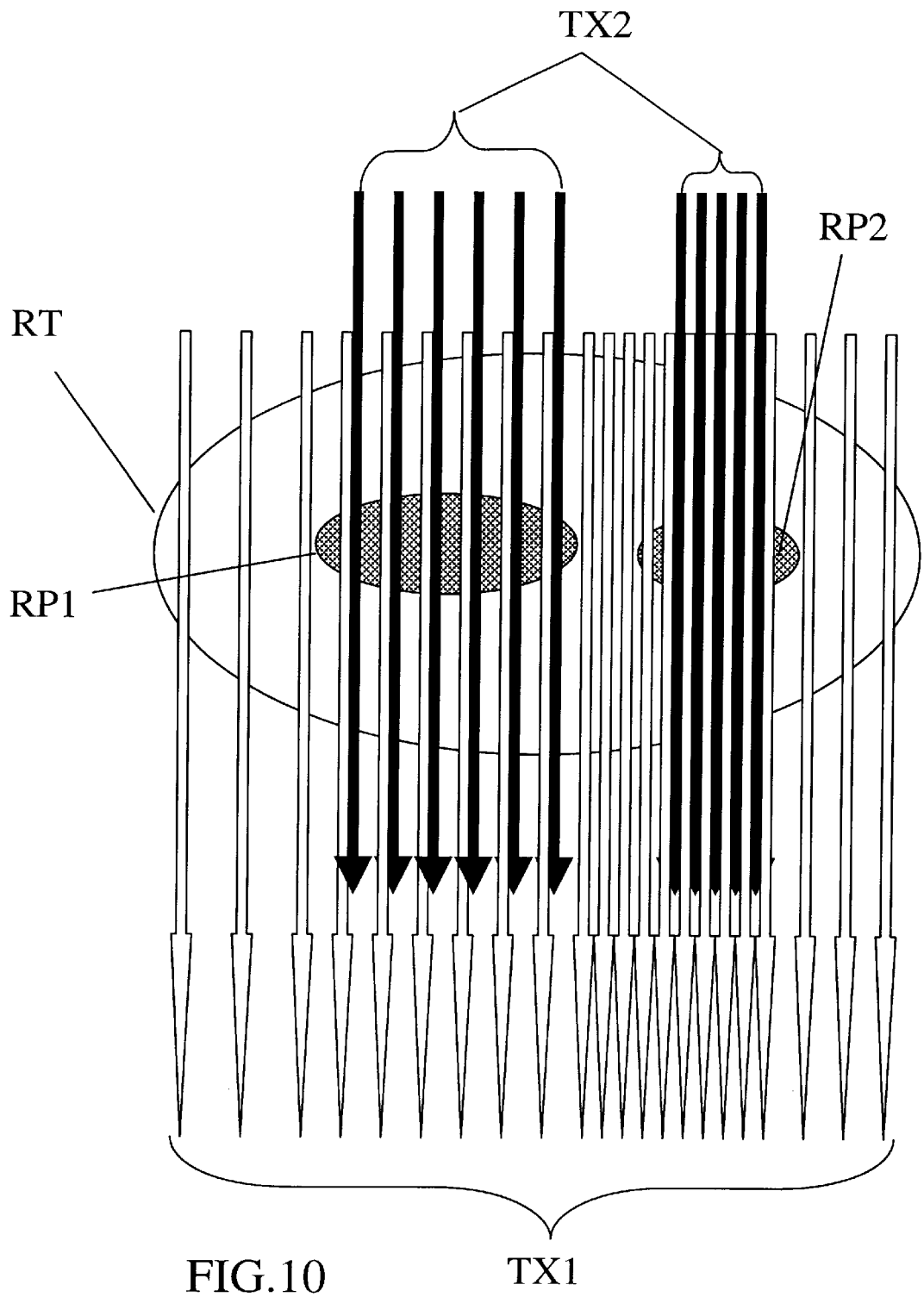
FIG. 10 is a diagram illustrating another embodiment of the method, in which different densities of scanlines and thus of projected beams are chosen for scanning different partial regions of the entire region under examination.

FIGS. 9 and 10 illustrates two different ways of illuminating the region under examination for carrying out the processing of the reflected beams according to at least two different processing or imaging modes.

In FIG. 9 it is considered that at least for a partial or limited zone RP of the region under examination instead of only one projected beam per each scan-line which projected beam is optimized for the processing the signals due to the corresponding reflected beams according to a first imaging or processing mode two subsequent projected beams are emitted for a same scan-line one of which TX1 is optimized for the first imaging mode and the second of which TX2 is optimized for the second processing or imaging mode.

Obviously when a limitation of the receiving signals along selected scan-lines is not considered two successive projected beams TX1 and TX2 may be emitted for each of the scan-lines forming the scan plane or slice.

This feature may be provided in combination with one or more of the features disclosed relating to the examples of FIGS. 4 to 8. Indeed more than only one partial zone may be present in the region under examination RT and different distributions of selected scan-lines associated to the second imaging mode may be chosen and also selected limited parts of the reflected beams may be treated according to the second imaging or processing mode. It may also be provided to emit only projected beams TX2 optimized for the second imaging mode along selected scan-lines particularly for those scan-lines crossing a chosen partial or limited zone RP and to process the related received signals according to only this second imaging or processing mode, while for the other scan-lines the projected beams are optimized for the first imaging mode and the processing of the received signals is carried out according this first imaging or processing mode.

Figure 8:
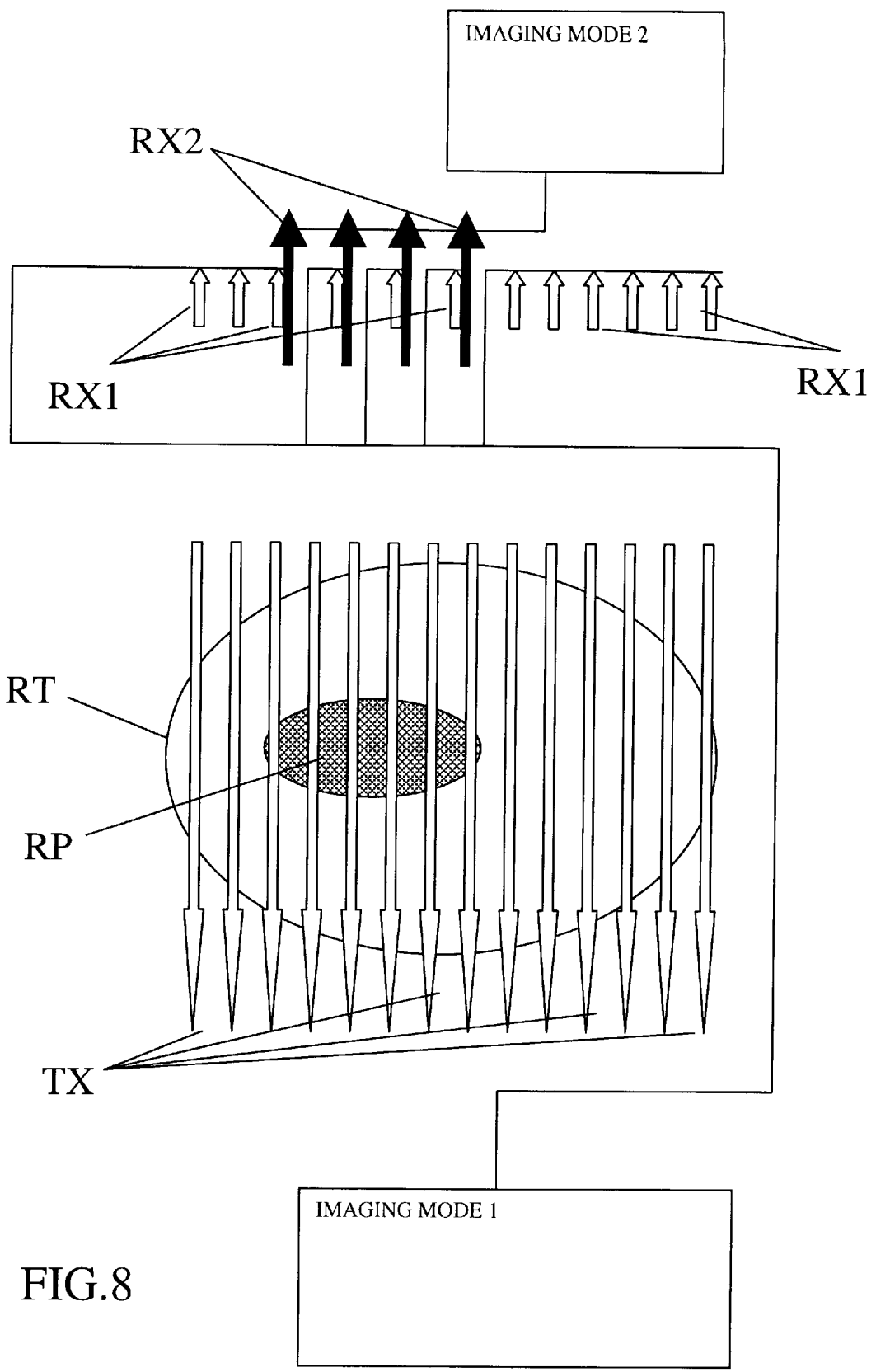
FIG. 8 is a diagram showing a first embodiment of the method in which only one ultrasound beam is fired for each scan-line forming a scan-plane or slice of the region under examination.

FIG. 8 show a different option according to which the projected beams TX are only of one kind for each scan-line and the corresponding processing beams are processed all or only for a selected part or group according to both imaging or processing modes.

FIG. 10 shows a further feature which may be provided separately or in combination with every one of the features described above with reference to the examples of FIGS. 4 to 9. In this case a different scan-line density or resolution is chosen for different zones of the egion under examination RT. The figure just depicts one pecial example but any kind of choice is possible. Being two partial or limited zones RP1 and RP2 present in the region under examination RT, the scan-lines are closer in these zones RP1 and RP2, while the scan-lines are spread apart at the border parts of the region under examination RT. In between the two limited zones RP1 and Rp2 the scan lines are closer. Furthermore the illustrated example shows two successive projected beams TX1 and TX2 optimized for respectively the first and the second imaging or processing mode along the scan-lines crossing the limited or partial zones RP1 and RP2, while along all the other scan-lines only one projected beam is considered which is optimized for the first processing or imaging mode, particularly a B-mode.

Alternatively only one projected beam can be emitted for each scan-line as explained with reference to FIG. 9. This way of scanning the region under examination can be combined with one or more of the features disclosed in the preceding examples according to FIGS. 4 to 9.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A Method for ultrasound imaging of tissues located in a tissue image region, comprising the steps of:
   a. Projecting at least one ultrasound beam into said tissue image region;
   b. Receiving ultrasound reflections of the said at least one ultrasound beam from said tissue image region and transducing said reflection into corresponding electric echo signals;
   c. Processing said echo signals according at least two different modes;
   d. One of said processing modes being an imaging mode furnishing a panoramic image of the region under examination
   e. The other at least further second processing mode being a different echo processing mode for imaging particular tissues or tissue structures or physiological flux;
   f. Displaying the images obtained by processing with the at least two modes in an interleaved or combined, particularly superimposed manner on the same screen;
   g. The image obtained by the first mode being displayed with a gray-scale;
   h. The image of the at least second processing mode being displayed in a colored manner by choosing a color adapted to the optimum physiological capability of human eyes to discriminate the information displayed by the color level scale.

2. A method according to claim 1, in which the color chosen is within the green to yellow wavelengths interval.

3. A Method according to claim 1, characterized in that the echo signals processed by the at least two different modes are due to the same at least one projected ultrasound beam for each scan-line.

4. A Method according to claim 1, characterized in that the at least two echo processing modes are executed in parallel or at the same time.

5. A Method according to claim 1, characterized in that the at least two echo processing modes are executed alternatively.

6. A Method according to claim 1, characterized in that the echo signals processed according to the at least two different modes are generated by reflection of a corresponding ultrasound beam which parameters are optimized for the corresponding modes.

7. A Method according to claim 6, characterized in that the at least two ultrasound beams are projected alternatively into said tissue imaging region.

8. A Method according to claim 1, characterized in that each image is formed by several adjacent scanning lines along a scanning section plane, said scanning lines being obtained by processing the echo signals generated by a ultrasound beam focussed on the said line according to the chosen mode.

9. A Method according to claim 8, characterized in that for each mode of the at least two processing modes a different number of scan-lines is chosen, with said received signals of the reflected beam along the said chosen scan-lines being processed according to the said imaging or processing mode.

10. A Method according to claim 9, characterized in that for a first imaging or processing mode the maximum possible number of scan lines are chosen, while for the at least second processing or imaging mode a reduced number of scan-lines is chosen either by limiting the density of the scan-lines or by limiting the width of the scan-region with respect to the maximum possible width of the region to be scanned.

11. A Method according to claim 9, characterized in that the received echo signals of at least part of one or more of said scan-lines are processed at least partly according to only one of the two processing modes and partly according to the other processing mode or according to a combination of the two processing modes by processing the time dependent signal of the reflected beam along the said scan-line with only one of the said two processing modes or with both modes for different parts corresponding to different or at least overlapping time periods of the duration of the reflected signal, which time periods corresponds to information reflected by tissues at different depth in the direction of the scan-line on which the projected beam has been focussed.

12. A Method according to claim 9, characterized that the first imaging or processing mode is a B-mode or an imaging mode using the information derived from the amplitude envelope of the echo signals received at a certain frequency while the at least second processing imaging mode is a mode using physical effects on the reflected echo signals such as frequency shifts or changes in the frequency spectra of the reflected echo signals.

13. A Method according to claim 9 characterized in that the at least second processing imaging mode is a mode using physical effects on the reflected echo signals is a Pulse Inversion imaging mode being provided two successive projected beams for each scanning line, the second beam being inverted with respect to the first beam.

14. A Method according to claim 9, characterized in that the at least second processing imaging mode is a mode using physical effects on the reflected echo signals is a Harmonic Imaging mode, wherein said echo signals received at a different frequency of the fundamental frequency of the projected ultrasound beam having extracted therefrom the part of said echo signals within a certain frequency spectrum or having a certain frequency different from the fundamental frequency of the ultrasound beam projected.

15. A Method according to claim 14, characterized in that the echo signals processed according to the at least second processing mode are the echo signals having an harmonic or sub harmonic frequency, particularly a frequency corresponding to the second harmonic of the fundamental frequency of the projected ultrasound beam.

16. A Method according to claim 1, characterized in that a contrast medium is injected into the tissues of the tissue imaging region.

17. A Method according to claim 1, characterized in that the image displayed is a weighted combination of the image processed with a first processing mode and of the image processed with at least a second processing mode.

18. A Method according to claim 17, characterized in that the weighted combination is of the kind: alpha*first-mode+(1-alphfa)*second-mode, where alpha has a value between 0 and 1.

19. A Method according to claim 17, characterized that the first processing mode is the B-mode and the second processing mode is a mode using physical effects on the reflected echo signals such as frequency shifts or changes in the frequency spectra of the reflected echo signals particularly a Harmonic Imaging mode, Pulse inversion mode, Pulse differentiation or subtraction mode, or Doppler modes.

20. A Method according to claim 1, in which the combination image obtained by the combination of the at least two processing modes is obtained by modulating some parameters of the image of a first processing mode by means of the informaton obtained from the at least one second processing mode.

21. A Method according to claim 20, characterized in that the image is displayed by means of HSV transforms, with H, S, V defined as a linear/non linear combination of one or two processing modes.

22. A Method according to claim 20, characterized in that the image is displayed by means of a Hue-Saturation-Value transform (HSV) by defining a constant Hue at a wavelength at which human eye's sensitivity is higher, particularly in the green to yellow wavelength range, and by modulating the Value by means of the information obtained with at least the first processing mode and by modulating the Saturation by means of the information obtained with the second processing mode.

23. A Method according to claim 22, characterized in that the Value is modulated by means of the combined information of the at least two processing modes, in particular according to the combination function of alpha*first-mode+(1-alpha)*second-mode, where alpha has a value between 0 and 1.

24. A Method according to claim 1, characterized in that a particular projected beam is used for exciting the said second imaging or processing mode in combination with the injection of contrast media in the tissue imaging region, the projected beam having a reduced or limited mechanical index at a level lower than the mechanical index needed to destroy or burst the contrast media micro bubbles.

25. A Method according to claim 1, characterized in that a HIS or a HLS palette is used for forming an image displaying at the same tile the information obtained from said first and said second processing modes.

26. A Method for ultrasound imaging of the evolution of contrast media enhancement or perfusion as a function of time providing the steps of firing successive ultrasound projected beams covering an interesting image area of the tissue imaging region and measuring the time between injection of contrast media and instant at which firing of the ultrasound projected beam occurred or the time passed between the firing of each subsequent projected beam along the same scan-line, the time measured being univocally correlated to each projected beam and to the corresponding reflected echo signal.

27. A Method according to claim 26, characterized in that the image data obtained due to the successive firing of projected beams correlated to the time interval passed from contrast media injection ad or from the preceding firing of the projected beam is stored in a memory, such that each time correlated image obtained and stored is displayed in a film like succession.

28. A Method according to claim 26, further comprising the steps of:

projecting at least one ultrasound beam into said tissue imaging region;

receiving ultrasound reflections of the said at least one ultrasound beam from said tissue image region and transducing said reflection into corresponding electric echo signals;

processing said echo signals according to at least two different modes, one of said processing modes being an imaging mode furnishing a panoramic image of the region under examination, another of said at least a second processing mode being a different echo processing mode for imaging particular tissues or tissue structures or physiological flux; and displaying the images obtained by processing with the at least two modes in an interleaved or combined, particularly superimposed manner on the same screen, the image obtained by the first mode being displayed with a gray-scale, the image of the at least second processing mode being displayed in a colored manner by choosing a color adapted to the optimum physiological capability of human eyes to discriminate the information displayed by the color level scale.

29. A method according to claim 28, in which the color chosen is within the green to yellow wavelengths interval.

30. A Method according to claim 28, characterized in that the echo signals processed by the at least two different modes are due to the same at least one projected ultrasound beam for each scan-line.

31. A Method according to claim 28, characterized in that the at least two echo processing modes are executed in parallel or at the same time.

32. A Method according to claim 28, characterized in that the at least two echo processing modes are executed alternatively.

33. A Method according to claim 28, characterized in that the echo signals processed according to the at least two different modes are generated by reflection of a corresponding ultrasound beam which parameters are optimized for the corresponding modes.

34. A Method according to claim 33, characterized in that the at least two ultrasound beams are projected alternatively into said tissue imaging region.

35. A Method according to claim 28, characterized that each image is formed by several adjacent scanning lines along a scanning section plane, said scanning lines being obtained by processing the echo signals generated by a ultrasound beam focussed on the said line according to the chosen mode.

36. A Method according to claim 35 characterized in that for each mode of the at least two processing modes a different number of scan-lines is chosen the received signals of the reflected beam along the said chosen scan-lines being processed according to the said imaging or processing mode.

37. A Method according to claim 36, characterized in that for a first imaging or processing mode the maximum possible number of scan lines are chosen, while for the at least second processing or imaging mode a reduced number of scan-lines is chosen either by limiting the density of the scan-lines or by limiting the width of the scan-region with respect to the maximum possible width of the region to be scanned.

38. A Method according to claim 36, characterized in that the received echo signals of at least part of one or more of said scan-lines is processed at least partly according to only one of the two processing modes and partly according to the other processing mode or according to a combination of the two processing modes by processing the time dependent signal of the reflected beam along the said scan-line with only one of the said two processing modes or with both modes for different parts corresponding to different or at least overlapping time periods of the duration of the reflected signal, which time periods corresponds to information reflected by tissues at different depth in the direction of the scan-line on which the projected beam has been focussed.

39. A Method according to claim 36, characterized in that the first imaging or processing mode is a B-mode or an imaging mode using the information derived from the amplitude envelope of the echo signals received at a certain frequency while the at least second processing imaging mode is a mode using physical effects on the reflected echo signals such as frequency shifts or changes in the frequency spectra of the reflected echo signals.

40. A Method according to claim 36, characterized in that the at least second processing imaging mode is a mode using physical effects on the reflected echo signals is a Pulse Inversion imaging mode being provided two successive projected beams for each scanning line, the second beam being inverted with respect to the first beam.

41. A Method according to claim 36, characterized in that the at least second processing imaging mode is a mode using physical effects on the reflected echo signals is a Harmonic Imaging mode, wherein said echo signals received at a different frequency of the fundamental frequency of the projected ultrasound beam having extracted therefrom the part of said echo signals within a certain frequency spectrum or having a certain frequency different from the fundamental frequency of the ultrasound beam projected.

42. A Method according to claim 41, characterized in that the echo signals processed according to the at least second processing mode are the echo signals having an harmonic or sub harmonic frequency, particularly a frequency corresponding to the second harmonic of the fundamental frequency of the projected ultrasound beam.

43. A Method according to claim 28, characterized in that a contrast medium is injected into the tissues of the tissue imaging region.

44. A Method according to claim 28, characterized in that the image displayed is a weighted combination of the image processed with a first processing mode and of the image processed with at least a second processing mode.

45. A Method according to claim 44, characterized in that the weighted combination is of the kind: alpha*first-mode+(1-alpha)* second-mode, where alpha has a value between 0 and 1.

46. A Method according to claim 28, in which the combination image obtained by the combination of the at least two processing modes is obtained by modulating some parameters of the image of a first processing mode by means of the information obtained from the at least one second processing mode.

47. A Method according to claim 46, characterized in that the image is displayed by means of HSV transform, with H, S, and V defined as a linear/non linear combination of one or two processing modes.

48. A Method according to claim 46, characterized in that the image is displayed by means of a Hue-Saturation-Value transform (HSV) by defining a constant Hue at a wavelength at which human eye's sensitivity is higher, particularly in the green to yellow wavelength range, and by modulating the Value by means of the information obtained with at least the first processing mode and by modulating the Saturation by means of the information obtained with the second processing mode.

49. A Method according to claim 48, characterized in that the Value is modulated by means of the combined information of the at least two processing modes, in particular according to the combination function of alpha*first-mode+(1-alpha)* second-mode, where alpha has a value between 0 and 1.

50. A Method according to claim 44, characterized in that the first processing mode is the B-mode and the second processing mode is a mode using physical effects on the reflected echo signals such as frequency shifts or changes in the frequency spectra of the reflected echo signals particularly a Harmonic Imaging mode, Pulse inversion mode, Pulse differentiation or subtraction mode, or Doppler mode.

51. A Method according to claim 26, characterized in that it provides the step of processing reflected echo signals of at least one projected ultrasound beam according to a first, a second and a third imaging or processing mode, being displayed at least two or three images relating to the combination of the information of the first and second processing mode and of the first and third processing mode and or of the second and third processing mode.

52. A Method according to claim 1, characterized in that it provides the step of processing reflected echo signals of at least one projected ultrasound beam according to a first, a second and a third imaging or processing mode, being displayed at least two or three images relating to the combination of the information of the first and second processing mode and of the first and third processing mode and or of the second and third processing mode.

53. A Method according to claim 52, characterized in that the three combination images are displayed alternatively according to automatic time sharing of the display monitor for each image or according to a manual selection of the user.

54. A Method according to claim 53, characterised in that at least two of the three combination images are displayed adjacent to one another in different areas of the display screen, while the third combination image is displayed alternatively with one of the first two images either by automatic time sharing of the display or by manual command.

55. A Method according to claim 52 characterized in that the three combination images are displayed at the same time in partial areas of the display screen.

56. A Method according to claim 52, characterized in that the first processing mode is a B-mode, the second processing mode is a Harmonic imaging mode or Pulse Inversion mode, the third processing mode is a Doppler or Color Doppler or Power Doppler mode.

57. A Method according to claim 56, characterized in that at least two of the three combination images are displayed relating to the combination of the information of the B-mode and of the Harmonic Imaging or Pulse inversion mode and according to the combination of information of the B-mode and the Doppler or Color Doppler or Power Doppler mode.

58. A Method according to claim 57, characterized in that a third image according to the combination of information of the Harmonic Imaging Mode or the Pulse Inversion Mode and of the information of the Doppler, or Color Doppler or Power Doppler mode is displayed either with the preceding two combination images or with one of the preceding two images, or alone.

59. A Method according to claim 58, characterized in that the image obtained by the Harmonic Imaging mode and or Pulse Inversion mode is displayed by a gray-scale palette, while the image of the Doppler, Color Doppler or Power Doppler mode is displayed by means of a color-scale palette.

60. A Method according to claim 59, characterized in that a combination of the three channels is made by means of a HSV transform.

61. A Method according to claim 60, characterized in that the combination image of the image information obtained by the Harmonic Imaging mode and or Pulse Inversion and of the image information obtained by the Doppler, Color Doppler or Power Doppler mode is displayed by means of a HSV transform being Hue a constant, the image information of the Harmonic Imaging mode and or Pulse Inversion mode modulating the Saturation while the Doppler, Color Doppler or Power Doppler mode modulates the value.

62. A Method according to claim 56, characterized in that the image information obtained by the Harmonic imaging mode and or pulse inversion and the image information obtained by the doppler, Color Doppler or Power Doppler mode are combined together by means of a weighted sum according to: alpha*first-mode+(1-alpha)*second-mode, where alpha has a value between 0 and 1.

63. A Method according to claim 61, characterized in that the Saturation is modulated by a weighted combination of the image information obtained by the Harmonic Imaging mode and or Pulse Inversion and the image information obtained by the Doppler, Color Doppler or Power Doppler mode according to: alpha*first-mode+(1-alpha)*second-mode, where alpha has a value between 0 and 1.

64. A Method according to claim 59, characterized in that a HIS or a HLS palette is used.

65. A Method according to claim 59, characterized in that the hue and or color is chosen in the wavelength interval from green to yellow.

66. A Method for ultrasound imaging, characterized in that in a tissue imaging region comprising arterial and venous blood vessels an image is displayed that is obtained by combining information processed according to B-Mode imaging of the tissue and information processed according to a second imaging or processing mode of the arterial blood flow, which image is compared to an image representing a combination of information obtained by B-Mode imaging of the tissue and information obtained by the second processing mode of the venous blood flow, and further characterised by acquiring contrast media perfusion behavior in the arteries and in the veins and by comparing said two behaviors with the behavior of other tissue kinds.

67. A Method according to claim 66, characterized in that successive groups of projected beams each one focussed on one of more scan lines covering a certain imaging region are fired for obtaining successive image information of a certain slice of the imaging region being each group of projected beams covering the selected image region preceded by a high energy projected beam with a mechanical index suitable for widely or completely destroying contrast media present in the said imaging region and by executing the firing of each group of projected beams with different step like longer lasting time periods from the firing of the preceding group of projected beams in order to acquire said perfusion behavior.

68. A Method according to claim 67 characterized in that a perfusion curve is measured for arterial and venous vessels.

69. A Method according to claim 67, characterized in that an automatic time basis is provided for automatically determining the moments of each successive group of projected and/or reflected beams covering a certain area of interest.

70. A Method according to claim 69, characterized in that the firing of each group is executed manually.

71. A Method according to claim 69, characterized in that the firing of each group is executed in an automatic way.

72. A Method according to claim 56, further comprising the steps of:
   projecting at least one ultrasound beam into said tissue imaging region;
   receiving ultrasound reflections of the said at least one ultrasound beam from said tissue image region and transducing said reflection into corresponding electric echo signals;
   processing said echo signals according to at least two different modes, one of said processing modes being an imaging mode furnishing a panoramic image of the region under examination, another of said at least a second processing mode being a different echo processing mode for imaging particular tissues or tissue structures or physiological flux; and
   displaying the images obtained by processing with the at least two modes in an interleaved or combined, particularly superimposed manner on the same screen, the image obtained by the first mode being displayed with a gray-scale, the image of the at least second processing mode being displayed in a colored manner by choosing a color adapted to the optimum physiological capability of human eyes to discriminate the information displayed by the color level scale.

73. A method according to claim 72, in which the color chosen is within the green to yellow wavelengths interval.

74. A Method according to claim 72, characterized in that the echo signals processed by the at least two different modes are due to the same at least one projected ultrasound beam for each scan-line.

75. A Method according to claim 72, characterized in that the at least two echo processing modes are executed in parallel or at the same time.

76. A Method according to claim 72, characterized in that the at least two echo processing modes are executed alternatively.

77. A Method according to claim 72, characterized in that the echo signals processed according to the at least two different modes are generated by reflection of a corresponding ultrasound beam which parameters are optimized for the corresponding modes.

78. A Method according to claim 77, characterized in that the at least two ultrasound beams are projected alternatively into said tissue imaging region.

79. A Method according to claim 72, characterized that each image is formed by several adjacent scanning lines along a scanning section plane, said scanning lines being obtained by processing the echo signals generated by a ultrasound beam focussed on the said line according to the chosen mode.

80. A Method according to claim 79, characterized in that for each mode of the at least two processing modes a different number of scan-lines is chosen the received signals of the reflected beam along the said chosen scan-lines being processed according to the said imaging or processing mode.

81. A Method according to claim 80, characterized in that for a first imaging or processing mode the maximum possible number of scan lines are chosen, while for the at least second processing or imaging mode a reduced number of scan-lines is chosen either by limiting the density of the scan-lines or by limiting the width of the scan-region with respect to the maximum possible width of the region to be scanned.

82. A Method according to claim 80, characterized in that the received echo signals of at least part of one or more of said scan-lines is processed at least partly according to only one of the two processing modes and partly according to the other processing mode or according to a combination of the two processing modes by processing the time dependent signal of the reflected beam along the said scan-line with only one of the said two processing modes or with both modes for different parts corresponding to different or at least overlapping time periods of the duration of the reflected signal, which time periods corresponds to information reflected by tissues at different depth in the direction of the scan-line on which the projected beam has been focussed.

83. A Method according to claim 80, characterized in that the first imaging or processing mode is a B-mode or an imaging mode using the information derived from the amplitude envelope of the echo signals received at a certain frequency while the at least second processing imaging mode is a mode using physical effects on the reflected echo signals such as frequency shifts or changes in the frequency spectra of the reflected echo signals.

84. A Method according to claim 80, characterized in that the at least second processing imaging mode is a mode using physical effects on the reflected echo signals is a Pulse Inversion imaging mode being provided two successive projected beams for each scanning line, the second beam being inverted with respect to the first beam.

85. A Method according to claim 80, characterized in that the at least second processing imaging mode is a mode using physical effects on the reflected echo signals is a Harmonic Imaging mode, wherein said echo signals received at a different frequency of the fundamental frequency of the projected ultrasound beam having extracted therefrom the part of said echo signals within a certain frequency spectrum or having a certain frequency different from the fundamental frequency of the ultrasound beam projected.

86. A Method according to claim 85, characterized in that the echo signals processed according to the at least second processing mode are the echo signals having an harmonic or sub harmonic frequency, particularly a frequency corresponding to the second harmonic of the fundamental frequency of the projected ultrasound beam.

87. A Method according to claim 72, characterized in that a contrast medium is injected into the tissues of the tissue imaging region.

88. A Method according to claim 72, characterized in that the image displayed is a weighted combination of the image processed with a first processing mode and of the image processed with at least a second processing mode.

89. A Method according to claim 88, characterized in that the weighted combination is of the kind: alpha*first-mode+(1-alpha)* second-mode, where alpha has a value between 0 and 1.

90. A Method according to claim 72, in which the combination image obtained by the combination of the at least two processing modes is obtained by modulating some parameters of the image of a first processing mode by means of the information obtained from the at least one second processing mode.

91. A Method according to claim 90, characterized in that the image is displayed by means of HSV transform, with H, S, and V defined as a linear/non linear combination of one or two processing modes.

92. A Method according to claim 90, characterized in that the image is displayed by means of a Hue-Saturation-Value transform (HSV) by defining a constant Hue at a wavelength at which human eye's sensitivity is higher, particularly in the green to yellow wavelength range, and by modulating the Value by means of the information obtained with at least the first processing mode and by modulating the Saturation by means of the information obtained with the second processing mode.

93. A Method according to claim 92, characterized in that the Value is modulated by means of the combined information of the at least two processing modes, in particular according to the combination function of alpha*first-mode +(1-alpha)* second-mode, where alpha has a value between 0 and 1.

94. A Method according to claim 88, characterized in that the first processing mode is the B-mode and the second processing mode is a mode using physical effects on the reflected echo signals such as frequency shifts or changes in the frequency spectra of the reflected echo signals particularly a Harmonic Imaging mode, Pulse inversion mode, Pulse differentiation or subtraction mode, or Doppler mode.

95. A Method according to claim 72, characterized in that a particular projected beam is used for exciting the said second imaging or processing mode in combination with the injection of contrast media in the tissue imaging region, the projected beam having a reduced or limited mechanical index at a level lower than the mechanical index needed to destroy or burst the contrast media micro bubbles.

96. A Method according to claim 72, characterized in that a HIS or a HLS palette is used for forming an image displaying at the same tile the information obtained from said first and said second processing modes.

97. A Method according to claim 56, further comprising the steps of firing successive ultrasound projected beams covering an interesting image area of the tissue imaging region and measuring the time between injection of contrast media and instant at which firing of the ultrasound projected beam occurred or the time passed between the firing of each subsequent projected beam along the same scan-line, the time measured being univocally correlated to each projected beam and to the corresponding reflected echo signal.

98. A Method according to claim 97, characterized in that the image data obtained due to the successive firing of projected beams correlated to the time interval passed from contrast media injection ad or from the preceding firing of the projected beam being stored in a memory, being each time correlated image obtained and stored displayed in a film like succession.

99. A Method according to claim 56, characterized in that in a tissue imaging region comprising arterial and venous blood vessels an image is displayed obtained by combining information processed according to B-Mode imaging of the tissue and information processed according to the second imaging or processing mode of the arterial blood flow which image is compared to an image representing a combination of information obtained by B-Mode imaging of the tissue and information obtained by the second processing mode of the venous blood flow.

100. A Method according to claim 56, characterized in that it provides the step of processing reflected echo signals of at least one projected ultrasound beam according to a first, a second and a third imaging or processing mode, being displayed at least two or three images relating to the combination of the information of the first and second processing mode and of the first and third processing mode and or of the second and third processing mode.

101. A Method according to claim 51, characterized in that the three combination images are displayed alternatively according to automatic time sharing of the display monitor for each image or according to a manual selection of the user.

102. A Method according to claim 100, characterized in that the three combination images are displayed alternatively according to automatic time sharing of the display monitor for each image or according to a manual selection of the user.

103. A Method according to claims 101, characterised in that at least two of the three combination images are displayed adjacent to one another in different areas of the display screen, while the third combination image is displayed alternatively with one of the first two images either by automatic time sharing of the display or by manual command.

104. A Method according to claims 102, characterised in that at least two of the three combination images are displayed adjacent to one another in different areas of the display screen, while the third combination image is displayed alternatively with one of the first two images either by automatic time sharing of the display or by manual command.

105. A Method according to claim 51, characterized in that the three combination images are displayed at the same time in partial areas of the display screen.

106. A Method according to claim 100, characterized in that the three combination images are displayed at the same time in partial areas of the display screen.

107. A Method according to claim 51, characterized in that the first processing mode is a B-mode, the second processing mode is a Harmonic imaging mode or Pulse Inversion mode, the third processing mode is a Doppler or Color Doppler or Power Doppler mode.

108. A Method according to claim 100, characterized in that the first processing mode is a B-mode, the second processing mode is a Harmonic imaging mode or Pulse Inversion mode, the third processing mode is a Doppler or Color Doppler or Power Doppler mode.

109. A Method according to claim 107, characterized in that at least two of the three combination images are displayed relating to the combination of the information of the B-mode and of the Harmonic Imaging or Pulse inversion mode and according to the combination of information of the B-mode and the Doppler or Color Doppler or Power Doppler mode.

110. A Method according to claim 108, characterized in that at least two of the three combination images are displayed relating to the combination of the information of the B-mode and of the Harmonic Imaging or Pulse inversion mode and according to the combination of information of the B-mode and the Doppler or Color Doppler or Power Doppler mode.

111. A Method according to claim 109, characterized in that a third image according to the combination of information of the Harmonic Imaging Mode or the Pulse Inversion Mode and of the information of the Doppler, or Color Doppler or Power Doppler mode is displayed either with the preceding two combination images or with one of the preceding two images, or alone.

112. A Method according to claim 110, characterized in that a third image according to the combination of information of the Harmonic Imaging Mode or the Pulse Inversion Mode and of the information of the Doppler, or Color Doppler or Power Doppler mode is displayed either with the preceding two combination images or with one of the preceding two images, or alone.

113. A Method according to claim 111, characterized in that the image obtained by the Harmonic Imaging mode and or Pulse Inversion mode is displayed by a gray-scale palette, while the image of the Doppler, Color Doppler or Power Doppler mode is displayed by means of a color-scale palette.

114. A Method according to claim 112, characterized in that the image obtained by the Harmonic Imaging mode and or Pulse Inversion mode is displayed by a gray-scale palette, while the image of the Doppler, Color Doppler or Power Doppler mode is displayed by means of a color-scale palette.

115. A Method according to claim 113, characterized in that a combination of the three channels is made by means of a HSV transform.

116. A Method according to claim 114, characterized in that a combination of the three channels is made by means of a HSV transform.

117. A Method according to claim 115, characterized in that the combination image of the image information obtained by the Harmonic Imaging mode and or Pulse Inversion and of the image information obtained by the Doppler, Color Doppler or Power Doppler mode is displayed by means of a HSV transform being Hue a constant, the image information of the Harmonic Imaging mode and or Pulse Inversion mode modulating the Saturation while the Doppler, Color Doppler or Power Doppler mode modulates the value.

118. A Method according to claim 116, characterized in that the combination image of the image information obtained by the Harmonic Imaging mode and or Pulse Inversion and of the image information obtained by the Doppler, Color Doppler or Power Doppler mode is displayed by means of a HSV transform being Hue a constant, the image information of the Harmonic Imaging mode and or Pulse Inversion mode modulating the Saturation while the Doppler, Color Doppler or Power Doppler mode modulates the value.

119. A Method according to claim 107, characterized in that the image information obtained by the Harmonic Imaging mode and or Pulse Inversion and the image information obtained by the Doppler, Color Doppler or Power Doppler mode are combined together by means of a weighted sum according to: alpha*first-mode+(1-alpha)*second-mode, where alpha has a value between 0 and 1.

120. A Method according to claim 108, characterized in that the image information obtained by the Harmonic Imaging mode and or Pulse Inversion and the image information obtained by the Doppler, Color Doppler or Power Doppler mode are combined together by means of a weighted sum according to: alpha*first-mode +(1-alpha)*second-mode, where alpha has a value between 0 and 1.

121. A Method according to claim 117, characterized in that the Saturation is modulated by a weighted combination of the image information obtained by the Harmonic Imaging mode and or Pulse Inversion and the image information obtained by the Doppler, Color Doppler or Power Doppler mode according to: alpha*first-mode+(1-alpha)*second-mode, where alpha has a value between 0 and 1.

122. A Method according to claim 118, characterized in that the Saturation is modulated by a weighted combination of the image information obtained by the Harmonic Imaging mode and or Pulse Inversion and the image information obtained by the Doppler, Color Doppler or Power Doppler mode according to: alpha*first-mode+(1-alpha)*second-mode, where alpha has a value between 0 and 1.

123. A Method according to claim 113, characterized in that a HIS or a HLS palette is used.

124. A Method according to claim 114, characterized in that a HIS or a HLS palette is used.

125. A Method according to claim 113, characterized in that the hue and or color is chosen in the wavelength interval from green to yellow.

126. A Method according to claim 114, characterized in that the hue and or color is chosen in the wavelength interval from green to yellow.

127. A device for ultrasound imaging comprising:
at least one ultrasound probe provided with at least one or with a linear or two-dimensional array of transducer transducing electric signal in ultrasound waves and impinging ultrasound waves in electric signals;
transmission beamformer for feeding to the transducer electric signal for generating projected ultrasound beams;
receiver beamformer for reconstructing from the reflected echo signals reflected echo beams;
at least two different processing channels according to at least two different processing modes for extracting/reconstructing displayable image information according to said two processing modes;
Means for combining the image information obtained by the said at least two processing modes;
Means for displaying the image information of the at least two processing modes one of the said image information with a gray-scale palette and the at least one further image information obtained by the at least one second processing mode with a color-scale palette.

128. A device for ultrasound imaging according to claim 127, characterized in that the color-scale palette is chosen within a wavelength interval for which the human eye's discrimination sensibility is a maximum.

129. A device according to claim 127, characterized in that the means for combining the image information obtained by the at least two processing modes determines a weighted combination of the image information of the at least two processing modes.

130. A device according to claim 129, characterized in that the weighted combination is determined according the following law:
Alphfa*first mode+(1-alpha)*second mode,
where alpha has a value between 0 and 1.

131. A device according to claim 127, characterized in that the image information relating to the first processing mode modulates the Saturation and the image information relating to the at least one second processing mode modulates the value of a HSV transform palette, while the Hue is chosen constant.

132. A device according to claim 127, characterized in that a timer is provided for calculating the time between two successive firing of a projected ultrasound beam.

133. A device according to claim 127, characterized in that a timer is provided for automatically executing the firing of two successive projected beams at certain time intervals one from the other.

134. A device according to claim 127, characterized in that a memory is provided for storing the image information according to at least one of the processing modes in an univocally correlated way to the time of firing or receiving the corresponding echo signal.

135. A device according to claim 127, characterized in that a transmission-beamformer and or a receiver-beamformer is provided for projected ultrasound beams and/or reflected echoes optimized for both the at least two processing modes.

136. A device according to claim 127, characterized in that a dedicated transmission beamformer and/or a dedicated receiver/beamformer is provided for projected ultrasound beams and or reflected echoes signals according to each of the at least two processing modes there being provided also a commutation unit for activating alternatively the said transmission/beamformer and or receiver/beamformer.

137. A device according to claim 127, characterized in that a timer unit is provided for firing groups of successive projected ultrasound beams, each of which beams of the said group is separated by a certain time interval, while a modulator unit is provided for switching and or regulating the power of the projected beams at a level of the mechanical index suitable for contrast agent destruction and at a level of mechanical index lower than the one needed to destroy contrast agents, further comprising timer means for generating at least a projected beam with power at a level of the mechanical index suitable for contrast agent destruction between firing of two successive groups of projected ultrasound beams.

138. A device according to claim 127, characterised in that manual command input means are provided for generating at least a projected beam with power at a level of the mechanical index suitable for contrast agent destruction between firing of two successive groups of projected ultrasound beams.

139. A device according to claim 127, characterised in that a third processing unit is provided for processing echo signals according to at least a third processing mode.

140. A device according to claim 127, characterized in that a first processing mode is a B-mode, while a second and or third processing mode is a Harmonic Imaging mode and or Pulse inversion mode, and or Doppler mode, and or Color Doppler mode and or Power Doppler mode, further comprising a processing unit for each of at least two of said modes.

141. A device according to claim 139, characterized in that a selecting unit is provided for activating the processing units according to at least two different processing modes and for combining the image information data of each one of the selected modes or of each possible permutation of two of the three processing modes.

142. A Device according to claim 127, characterised in that means are provided for processing a certain number of the scan-lines with one of the processing modes.

143. A device according to claim 127, characterised in that means are provided for processing only a certain part of a certain number of scan-lines with one of the two processing modes, said certain part corresponding to a certain time interval of the reflected beam along a certain scan-line which corresponds to a certain depth range along said scan-line.

144. A Device according to claim 141, characterised in that the other scan lines or the other parts of each scan line corresponding to other time intervals of the reflected echo signal along the said scan line are processed according to another processing mode or to a combination of the processing modes.

* * * * *